(12) United States Patent
Kavazanjian et al.

(10) Patent No.: US 11,987,741 B2
(45) Date of Patent: May 21, 2024

(54) BIOCEMENTATION SYSTEMS AND METHODS

(71) Applicant: ARIZONA BOARD OF REGENTS ON BEHALF OF ARIZONA STATE UNIVERSITY, Scottsdale, AZ (US)

(72) Inventors: Edward Kavazanjian, Tempe, AZ (US); Nasser Hamdan, Scottsdale, AZ (US); Hamed Khodadadi Tirkolaei, Tempe, AZ (US); Abdullah Almajed, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 597 days.

(21) Appl. No.: 17/192,337

(22) Filed: Mar. 4, 2021

(65) Prior Publication Data
US 2021/0189238 A1   Jun. 24, 2021

Related U.S. Application Data

(63) Continuation of application No. PCT/US2019/050474, filed on Sep. 10, 2019.
(Continued)

(51) Int. Cl.
*C09K 17/44*  (2006.01)
*C04B 24/14*  (2006.01)
(Continued)

(52) U.S. Cl.
CPC ............. *C09K 17/44* (2013.01); *C04B 24/14* (2013.01); *C04B 28/003* (2013.01); *E02D 3/12* (2013.01); *C04B 2103/0001* (2013.01); *C04B 2111/00732* (2013.01); *C12Y 305/01005* (2013.01); *E02D 2300/0025* (2013.01); *E02D 2300/0045* (2013.01)

(58) Field of Classification Search
None
See application file for complete search history.

(56) References Cited

U.S. PATENT DOCUMENTS 1,002,204 A   1/1977   Cavin et al.
4,002,204 A   1/1977   Cavin
(Continued)

FOREIGN PATENT DOCUMENTS

JP   2011157700   8/2011
KR   10-2012-1141978   5/2012
(Continued)

OTHER PUBLICATIONS

USPTO, Office Action dated Aug. 30, 2023 with U.S. Appl. No. 17/411,590.
(Continued)

*Primary Examiner* — John J Figueroa
(74) *Attorney, Agent, or Firm* — Snell & Wilmer L.L.P

(57) ABSTRACT

The present disclosure provides a method of biocementation comprising contacting a granular, cohesionless soil with a solution, wherein the solution comprises urea, urease, a source of calcium ions, and a source of non-urease proteins, wherein the urea, urease, source of calcium ions, and source of non-urease proteins are provided in effective amounts suitable to cause crystallization of calcium carbonate.

8 Claims, 25 Drawing Sheets

Related U.S. Application Data

(60) Provisional application No. 62/729,221, filed on Sep. 10, 2018.

(51) Int. Cl.
  *C04B 28/00*   (2006.01)
  *C04B 103/00*  (2006.01)
  *C04B 111/00*  (2006.01)
  *E02D 3/12*    (2006.01)

(56) References Cited

U.S. PATENT DOCUMENTS

| | | | |
|---|---|---|---|
| 5,143,155 | A | 9/1992 | Ferris et al. |
| 5,670,567 | A | 9/1997 | Lahalih |
| 5,730,873 | A | 3/1998 | Hapka et al. |
| 5,824,725 | A | 10/1998 | Lahalih |
| 7,841,804 | B2 | 11/2010 | Ostvold |
| 8,182,604 | B2 | 5/2012 | Kucharski et al. |
| 8,401,819 | B2 | 3/2013 | Kavaklioglu et al. |
| 8,420,352 | B2 | 4/2013 | Crawford et al. |
| 8,420,362 | B2 | 4/2013 | Crawford et al. |
| 9,850,379 | B2 | 12/2017 | Li et al. |
| 10,392,767 | B2 | 8/2019 | Kavazanjian et al. |
| 10,399,130 | B2 | 9/2019 | Halden et al. |
| 10,563,233 | B2 | 2/2020 | Kavazanjian et al. |
| 10,724,198 | B2 | 7/2020 | Kavazanjian et al. |
| 10,794,029 | B2 | 10/2020 | He et al. |
| 11,274,323 | B2* | 3/2022 | Kavazanjian ............ C12P 3/00 |
| 2002/0156337 | A1 | 10/2002 | Jensen et al. |
| 2007/0204990 | A1 | 9/2007 | Kollar |
| 2012/0169584 | A1 | 10/2012 | Ostvold |
| 2012/0308306 | A1 | 12/2012 | Kruse et al. |
| 2015/0299975 | A1 | 10/2015 | Li et al. |
| 2016/0236943 | A1* | 8/2016 | Kavazanjian ............ C02F 1/42 |
| 2016/0236949 | A1 | 8/2016 | Sage-Passant |
| 2016/0244931 | A1 | 8/2016 | Kavazanjian |
| 2016/0264463 | A1 | 9/2016 | Dosier et al. |
| 2017/0029689 | A1 | 2/2017 | Wilson et al. |
| 2018/0119185 | A1 | 5/2018 | Kavazanjian |
| 2019/0256770 | A1* | 8/2019 | He ............................ E02D 3/12 |
| 2019/0382976 | A1 | 12/2019 | Kavazanjian |
| 2020/1766130 | | 9/2020 | Kavazanjian et al. |
| 2020/0340021 | A1 | 10/2020 | Kavazanjian et al. |

FOREIGN PATENT DOCUMENTS

| | | |
|---|---|---|
| WO | 1998/000530 | 1/1998 |
| WO | 1999/005394 | 2/1999 |
| WO | 2005/124100 | 12/2005 |
| WO | 2006/066326 | 12/2005 |
| WO | 2007/064213 | 6/2007 |
| WO | 2008/119620 | 9/2008 |
| WO | 2011/078690 | 6/2010 |
| WO | 2013/120847 | 8/2013 |
| WO | 2015065951 | 5/2015 |
| WO | 2015065963 | 5/2015 |
| WO | 2017015230 | 1/2017 |
| WO | 2017139750 | 8/2017 |
| WO | 2020055915 | 3/2020 |
| WO | 2020176613 | 9/2020 |

OTHER PUBLICATIONS

USPTO Notice of Allowance dated Dec. 22, 2021 in U.S. Appl. No. 16/782,361.
USPTO Notice of Allowance dated Mar. 16, 2020 in U.S. Appl. No. 16/077,435.
USPTO Supplemental Notice of Allowability dated May 5, 2020 in U.S. Appl. No. 16/077,435.
USPTO Notice of Allowance dated Jul. 15, 2020 in U.S. Appl. No. 16/077,435.
USPTO, Restriction Requirement dated Mar. 31, 2023 with U.S. Appl. No. 17/411,590.
Talukdar et al., "Swelling and drug release behaviour of xanthan gum matrix tablets." Inter. J. of Pharmaceutics, 1995, 120(1 ), pp. 63-72.
Tanaka et al., "Use of fall cone test as measurement of shear strength for soft clay materials." Soils and Foundations J012, 52, pp. 590-599.
United States Environmental Protection Agency, Counties Designated "Nonattainment" Green Book, http://www3.epa.gov/airquality/greenbook/mapnpoll.html.
Van Humbeck et al., "Ammonia capture in porous organic polymers densely functionalized with brimsted acid groups." Journal of the American Chemical Society 2014, 136, pp. 2432-2440.
Van Oss et al., "Cement manufacture and the environment part II: environmental challenges and opportunities." Journal of Industrial Ecology 2003, 7, pp. 93-126.
Van Oss et al., "Cement manufacture and the environment: part I: chemistry and technology." Journal of Industrial Ecology 2002, 6, pp. 89-105.
Woolard et al., "Treatment of hypersaline wastewater in the sequencing batch reactor." Water Research 1995, 29, pp. 1159-1168.
Wu et al., "Effect of cross-linking on the diffusion of water, ions, and small molecules in hydrogels." The Journal of Physical Chemistry B 2009, 113, pp. 3512-3520.
"Yasuhara et al., Experiments and predictions of physical properties of sand cemented by enzymatically-induced :: carbonate precipitation." Soils and Foundations 2012, 52, pp. 539-549.
Zheng et al., "Evaluation of ammonium removal using a chitosan-g-poly {acrylic acid)/rectorite hydrogel composite." Journal of hazardous materials 2009, 171, pp. 671-677.
Zobeck,"Soil properties affecting wind erosion." Journal of Soil and Water Conservation 1991, 46, pp. 112-118.
Burbank, M., et al.. (2012). Geotechnical tests of sands ollowing bioinduced calcite precipitation catalyzed by indigenous bacteria. J. Geotech. Geoenviron. Engng 139, No. 6, 928-936.
DeJong, J.T., et al.. (2013). Bio-mediated soil improvement field study to stabilize mine sands. Proceedings of GeoMontreal 2013, Montreal, Canada.
Greely, R., et al. (1980). Threshold windspeeds for sand on mars: wind tunnel imulations. Geophys. Res. Lett. 7, No. 2, 121-124.
Van Paassen. L.A., et al.(2010). "Potential Soil Reinforcement by Biological Dentrification." Ecological Engineering, V 36(2): 168-175.
Almajed, Abdullah, et al. (2018). "Enzyme Induced Biocementated Sand with High Strength at Low Carbonate :; ontenl."
Ivanov, V. et al.(2008). Applications of microorganisms to geotechnical engineering for bioclogging and biocementation of soil in situ. Rev. Environ. Sci. Biotechnol. &, No. 2, 139-153.
Kavazanjian, E. et al. (2008). Microbiological improvement of the physical properties of soil. Proceedings of 6th international conference on case histories in geotechnical engineering, Rolla, MO, USA, pp. 58-66.
Faschingleitner et al., "Evaluation of primary and secondary fugitive dust suppression methods using enclosed water , praying systems at bulk solids handling," Advanced Powder Technology, 22, 2011, pp. 236-244.
Van Paassen, L.A., et al. (2010). :Quantifying biomediated ground improvement by ureolysis: large-scale biogrout experiment. J. Geotech. Geoenviron. Engng 136, No. 12, 1721-1728.
Williams, D.A. et al. (2013). NASA's planetary aeolian laboratory: exploring aeolian precesses on earth, mars, and titan. Proceedings of the 44th lunar and planetary science conference, Houston, TX, USA.
Das, N., et al. (2002) "Purification and Characterization of Urease from Dehusked Pigeonpea Seeds" Phytochemistry 61 (5) 513-521.
He, J., et al..(2013) "Mitigation of Liquefaction of Saturated Sand using Biogas," Geotechnique, 63(4) 367-275.
Martinez, B.C., et al. (2013)Experimental Optimization of Microbial-induced Carbonate Precipitation for Soil Improvement, Journal of Geotechnical and Geoenviron mental Engineering, V 139: 587-598.
Angers et al., "Plant-induced changes in soil structure: processes and feedbacks." Biogeochemistry 42.1-2, 1998, pp. 55-72.

(56) References Cited

OTHER PUBLICATIONS

Anseth et al. "In situ forming degradable networks and their application in tissue engineering and drug delivery." J. Control. Release, 78(1), 2002, pp. 199-209.
Bercea et al., "Dextran-Based Polycations: Thermodynamic Interaction with Water as Compared With Unsubstituted Dextran, 2-Flory/Huggins Interaction Parameter." Macromolecular Chemistry and Physics 212.17, 2011, pp. 1932-1940.
Stern et al., "Economic growth and environmental degradation: the environmental Kuznets curve and sustainable : development." World Development 1996, 24, pp. 1151-1160.
Chudzikowski "Guar gum and its applications." J Soc. Cosmet. Chem., 22, 1971, pp. 43-60.
Borja, "Condition for liquefaction instability in fluid-saturated granular soils", Acta Geotechnica 2006, 1, pp. 211-224.
Braissant, et al. "Bacterially induced mineralization of calcium carbonate in terrestrial environments: the role of exopolysaccharides and amino acids." J_ of Sedimentary Research, 73(3), 2003, pp. 485-490.
Chen et al., "Removal of heavy metal ions by a chelating resin containing glycine as chelating groups", Separation and purification technology 2007, 54, pp. 396-403.
Chen et al., "Biopolymer stabilization of mine tailings." J.Geotech. and Geoenviron. Eng., 139(10), 2013, pp. 1802-1807.
Watson et al., Air pollution engineering manual 2nd Edition, Wiley-Interscience, Hoboken, 2000, pp. 117-135.
Decho "Overview of biopolymer-induced mineralization: what goes on in biofilms?" Ecological Engineering 36.2, 2010, pp. 137-144.
DeJong et al., "Biogeochemical processes and geotechnical applications: progress, opportunities and challenges." Geotechnique, 63(4), 2013, pp. 287-301.
Dejong, J. T. et al. "Bio-mediated soil improvement." Ecological Engineering, 2010, vol. 36, pp. 197-210.
Demitri et al., "Potential of cellulose-based superabsorbent hydrogels as water reservoir in agriculture", International Journal of Polymer Science 2013, 2013.
Doussan et al., Water uptake by plant roots: II-modelling of water transfer in the soil root-system with explicit account of flow within the root system-comparison with experiments, Plant and soil 283. 1-2, 2006, pp. 99-117.
Eliassi et al., "Measurement of activity of water in aqueous poly-(ethylene glycol) solutions (effect of excess volume on the Flory-Huggins x-parameter)." J. Chem. Eng. Data, 44(1), 1999, pp. 52-55.
Emerson et al., "Determination of solvent-polymer and polymer-polymer Flory-Huggins interaction parameters for Joly (3-hexylthiophene) via solvent vapor swelling." Macromolecules, 46(16), 2013, pp. 6533-6540.
Ercole et al., "Bacterially induced mineralization of calcium carbonate: the role of exopolysaccharides and capsular Jolysaccharides." Microscopy and Microanalysis, 13(01), 2007, pp. 42-50.
Estroff et al., "An organic hydrogel as a matrix for the growth of calcite crystals." Org. Biomol. Chem., 2(1 ), 2004, pp. 137-141.
USPTO; Final Office Action in the U.S. Appl. No. 16/782,361 dated Jun. 3, 2021.
USPTO; Restriction Requirement in the U.S. Appl. No. 15/803,700 dated Jul. 12, 2018.
USPTO; Non-Final Office Action in the U.S. Appl. No. 15/803,700 dated Mar. 1, 2019.
USPTO; Notice of Allowance in the U.S. Appl. No. 15/803,700 dated Oct. 23, 2019.
Al Qabany et al., "Microbial Carbonate Precipitation: Correlation of S-Wave Velocity with Calcite Precipitation", Geo-Frontiers, pp. 3993-4001 (2011).
Al Qabany et al., "Factors Affecting Efficiency of Microbially Induced Calcite Precipitation", J. Geotech. Geoenviron. Eng., 138, pp. 992-1001 (2012).
Ozdogan et al., "A study on the triaxial shear behavior and microstructure of biologically treated sand specimens", University of Delaware, (2010).

Bang et al., "Application of Novel Biological Technique in Dust Suppression", TRB 2009 Annual Meeting (2009).
Barksdale et al., "Design, Construction and Testing of Sand Compaction Piles", ASTM Special Technical Publication, pp. 4-18 (1991).
Blakeley et al., "Jack Bean Urease: the First Nickel Enzyme", Journal of Molecular Catalysis, 23, pp. 263-292 (1984).
Chou et al., "Biocalcification of Sand through Ureolysis", J. Geotech. Geoenviron. Eng., 137, pp. 1179-1189 (2011).
Das et al., "Purification and characterization of urease from dehusked pigeonpea {*Cajanus cajan* L.) seeds", Dhytochemistry, 61, pp. 513-521 (2002).
Dejong et al., Microbially Induced Cementation to Control Sand Response to Undrained Shear, . Geotech. 3eoenviron. Eng., 132, pp. 1381-1392 (2006).
Farouz et al., "Evaluation of Axial Capacity of Post Grouted Drilled Shafts", GeoShanghai 2010 International Conference, pp. 216-223 (2010).
Germishuizen et al., "A laboratory study of soil stabilisation with a urea-formaldehyde resin", Journal of the South African Institution of Civil Engineering, 44, pp. 9-12 (2002).
Hamdan et al., "Carbonate Mineral Precipitation for Soil Improvement through Microbial Denitrification", Geo-Frontiers 2011, pp. 3925-3934 (2011).
Harkes et al., "Fixation and distribution of bacterial activity in sand to induce carbonate precipitation for ground reinforcement", Ecological Engineering, 36, pp. 112-117 (2010).
Ivanov et al., "Applications of microorganisms to geotechnical engineering for bioclogging and biocementation of soil in situ", Rev Environ Sci Biotechnol, 7, pp. 139-153 (2008).
Jabri et al., Preliminary crystallographic studies of urease from jack bean and from Klebsiella aerogenes, Journal of Molecular Biology, 227, pp. 934-937 (1992).
King et al., "Post Grouted Drilled Shafts—A Comprehensive Case History from Texas", Contemporary Topics in Deep Foundations, pp. 31-38 (2009).
Marzadori et al., "Immobilization of Jack Bean Urease on Hydroxyapatite: Urease Immobilization in Alkaline Soils", Soil Biology and Biochemistry, 30, pp. 1485-1490 (1998).
Mullins et al., "Predicting End Bearing Capacity of Post-Grouted Drilled Shafi in Cohesionless Soils", Journal of Geotechnical and Geoenvironmental Engineering, 132, pp. 478-487 (2006).
Ng et al., "An Overview of the Factors Affecting Microbial-Induced Calcite Precipitation and its Potential Application in Soil Improvement", World Academy of Science, Engineering and Technology, 62, pp. 723-729 (2012).
Ni et al., "Pervious Concrete Pile: An Innovation Ground Improvement Alternative", Geo-Congress 2013, pp. 2058-2065 (2013).
Pettit et al., "Soil Urease: Activity, Stability and Kinetic Properties", Soil Biology and Biochemistry, 8, pp. 479-484 (1976).
Siddik et al., "Effect of bacterial calcium carbonate precipitation on the geotechnical properties of soils", 2nd International Balkans Conference on Challenges of Civil Engineering, BCCCE, pp. 802-809 (2013).
Sumathi et al., "Impact of indigenous microorganisms on soil microbial and enzyme activities", Scholars Research Library, Archives of Applied Science Research, 4, pp. 1065-1073 (2012).
Van Paassen et al., "Quantifying Biomediated Ground Improvement by Ureolysis: Large-Scale Biogrout Experiment", J. Geotech. Geoenviron. Eng., 136, pp. 1721-1728 (2010).
Whiffin et al., "Microbial Carbonate Precipitation as a Soil Improvement Technique", Geomicrobiology Journal, 24, pp. 417-423 (2007).
USPTO; Restriction Requirement in the U.S. Appl. No. 15/029,316 dated Feb. 21, 2018.
USPTO; Non-Final Office Action in the U.S. Appl. No. 15/029,316 dated Dec. 12, 2018.
USPTO; Notice of Allowance in the U.S. Appl. No. 15/029,316 dated Jun. 19, 2019.
PCT; International Search Report and Written Opinion in the PCT Application No. PCT/US2014/062557 dated Feb. 12, 2015.
PCT; International Search Report and Written Opinion in the PCT Application No. PCT/US2014/062540 dated Feb. 9, 2015.

(56) References Cited

OTHER PUBLICATIONS

Hamdan et al., "Sequestration of Radionuclides and Metal Contaminants through Microbially-Induced Carbonate Precipitation", 2011 Pan-Am CGS Geotechnical Conference, (2011).

Hamdan et al., "Carbonate Cementation via Plant Derived Urease," Proceedings of the 18th International Conference on Soil Mechanics and Geotechnical Engineering, Paris 2013.

PCT; International Search Report and Written Opinion in the PCT Application No. PCT/US2019/50474 dated Jan. 9, 2020.

Schlumberger, "Unconfined compressive strength, " Feb. 3, 2017, retrieved on Dec. 16, 2019 from https://web.archive.org/web/20170203220634/https://www.glossary.oilfield.slb.com/en/terms/u/unconfined_ compressive_ strength .aspx.

USPTO; Notice of Allowance in the U.S. Appl. No. 15/029,866 dated Mar. 23, 2020.

USPTO; Restriction Requirement in the U.S. Appl. No. 15/029,866 dated Mar. 7, 2018.

USPTO; Non-Final Office Action in the U.S. Appl. No. 15/029,866 dated Jan. 11, 2019.

USPTO; Final Office Action in the U.S. Appl. No. 15/029,866 dated Jul. 10, 2019.

USPTO; Non-Final Office Action in the U.S. Appl. No. 16/782,361 dated Sep. 30, 2020.

U.S. Appl. No. 17/192,337, filed Mar. 4, 2021, Kavazanjian et al.

Fernando et al., "Forecasting PM10 in metropolitan areas: Efficacy of neural networks." Environmental pollution 163, 2012, pp. 62-67.

Fu et al., "Thermochemistry and kinetics of chemical polymerization of aniline determined by solution calorimetry." Chemistry of materials 6.5, 1994, pp. 671-677.

Galan-Marin et al., "Clay-based composite stabilized with natural polymer and fibre." Construction and Building Materials 2010, vol. 24, pp. 1462-1468.

Garrigues et al., Water uptake by plant roots: I-Formation and propagation of a water extraction front in mature root systems as evidenced by 2D light transmission imaging. Plant and Soil 2006, 283, pp. 83-98.

Sciarra et al., "Soil-gas survey of liquefaction and collapsed caves during the Emilia seismic sequence." Annals of Geophysics 2012, 55.

Hoffmann, "Conventional and Environmentally-sensitive Hydrogels for Medical and Industrial Uses: A Review Paper." Polymer Gels, 1991, pp. 289-297.

Jones et al., "Effects of temperature, pH, salinity, and inorganic nitrogen on the rate of ammonium oxidation by nitrifiers isolated from wetland environments." Microbial Ecology 1980, 6, pp. 339-347.

Karraker et al., "Impacts of road deicing salt on the demography of vernal pool-breeding amphibians." Ecological applications 2008, 18, pp. 724-734.

Kavazanjian E. and Hamdan N. (2015). "Enzyme induced carbonate precipitation (EICP) columns for ground mprovement." Proc. of the 2015 ASCE Geo-Institute GeoCongress, San Antonio, Texas.

Kherb et al., "Role of carboxylate side chains in the cation Hofmeister series." The Journal of Physical Chemistry B J012, 116, pp. 7389-7397.

Kim et al., "Hydrogel-actuated integrated responsive systems (HAIRS): Moving towards adaptive materials." Current : Opinion in Solid State and Materials Science 2011, 15, pp. 236-245.

Lambers, H. "Introduction, dryland salinity: a key environmental issue in southern Australia." Plant and Soil 2003, 257, v-ii.

Maghchiche et al., "Use of polymers and biopolymers for water retaining and soil stabilization in arid and semiarid egions." Journal of Taibah University for Science 2010, 4, pp. 9-16.

McKenna Neuman et al., Wind tunnel simulation of environmental controls on fugitive dust emissions from mine ailings. Atmospheric Environment 2009, 43, pp. 520-529.

Mehta, "Reducing the environmental impact of concrele." Concrele international 2001, 23, pp. 61-66.

Meyer et al., "Microbiologically-Induced Soil Stabilization: Application of Sporosarcina pasteurii for Fugitive Dust :; onlrol." Proc. of the 2011 ASCE Geo-Frontiers, Advances in Geotechnical Engineering, 2011, pp. 4002-4011.

Monlux et al., U.S. Department of Agriculture, Forest Service, National Technology and Development Program J6771805-SDTDC, 2006, 1-23.

Nemati et al. "Modification of porous media permeability, using calcium carbonate produced enzymatically in situ." Enzyme and Microbial Technology 2003, 33, pp. 635-642.

Neupane et al., Soil Improvement through enzymatic calcite precipitation technique: small to large scale experiments. nl. J. Lsld. Env. 2013, 1, pp. 65-66.

Neupane et al., "Applicability of enzymatic calcium carbonate precipitation as a soil-strengthening technique." Journal of Geotechnical and Geoenvironmental Engineering, 2013, vol. 139, pp. 2201-2211.

Oades et al., Australian Journal of Soil Research 1991, 29, 815-828.

Orts et al., J. Maler. Civ. Eng. 2007, 19, pp. 58-66.

Prusinski et al., "Effectiveness of Portland cement and lime in stabilizing clay soils." Transportation Research Record: Journal of the Transportation Research Board 1999, 1652, pp. 215-227.

U.S. Appl. No. 13/944,450, filed Jul. 17, 2013, Kavazanjian et al.

Greeley, R., White, B.R., Pollack, J.B., Iversen, J.D. & Leach, R.N. (1981). Dust storms on mars: considerations and simulations. Geol. Soc. Am. Special Papers 186, 101-122.

Korean Intellectual Property Office; PCT International Search Report, issued in connection to PCT/US2017017649 dated May 22, 2017.

Korean Intellectual Property Office; Written Opinion International Search Authority, issued in connection to PCT/US 2017017649 dated May 22, 2017.

Mohamed et al. "Purification of urease from water melon seeds for clinical diagnostic kits" (Bioresource Tech, 68, 1999, 215-223).

* cited by examiner

BIOCEMENTATION SYSTEMS AND METHODS

CROSS-REFERENCE TO RELATED APPLICATIONS

This application is a continuation of PCT Application No. PCT/US2019/050474 filed on Sep. 10, 2019 and entitled BIOCEMENTATION SYSTEMS AND METHODS. PCT Application No. PCT/US2019/050474 claims priority to, and the benefit of, U.S. Provisional Application No. 62/729,221 filed on Sep. 10, 2018 and entitled BIOCEMENTATION SYSTEMS AND METHODS. The disclosures of all the foregoing applications are incorporated herein by reference in their entireties, including but not limited to those portions that specifically appear hereinafter, but except for any subject matter disclaimers or disavowals, and except to the extent that the incorporated material is inconsistent with the express disclosure herein, in which case the language in this disclosure shall control.

STATEMENT OF U.S. GOVERNMENT INTEREST

This invention was made with government support under grant number 1449501 awarded by the National Science Foundation. The government has certain rights in the invention.

TECHNICAL FIELD

The present disclosure relates generally to biocementation systems and methods and, more specifically, to systems and methods of increasing the strength of biocemented sand.

BACKGROUND

Biologically based calcium carbonate precipitation is under investigation as a sustainable binder for granular soils, a process sometimes referred to as biocementation. Carbonate precipitation via hydrolysis of urea is one technique that has been investigated by geotechnical researchers. This technique utilizes the urease enzyme to catalyze the hydrolysis of urea in an aqueous solution, causing alkalinity and forming carbonate ions that leads to calcium carbonate precipitation in presence of calcium ions. One method of carbonate precipitation via hydrolysis of urea employs ureolytic microbes (microbes containing intracellular urease) as the source of urease and is referred to as microbially induced carbonate precipitation (MICP). Another method of carbonate precipitation uses agriculturally-derived free urease enzyme as the source of urease, a process referred to as enzyme induced carbonate precipitation (EICP).

Effectiveness of soil improvement via carbonate precipitation is typically measured by the unconfined compressive strength of the soil. Using conventional EICP techniques, multiple cycles of EICP treatment and/or more concentrated substrate or enzyme formulations may be required to achieve the desired compressive strength of improved soil. Field applications of EICP for engineering purposes may require a kilogram-scale supply of urease, making the cost of free urease enzyme a barrier to practical application. Additionally, undesirable ammonium chloride may result from conventional EICP treatment. Accordingly, improved methods for biocementation remain desirable.

SUMMARY

Methods of biocementation are disclosed herein. The methods may comprise contacting a granular, cohesionless soil with a solution comprising urea, urease, a source of calcium ions, and a source of non-urease proteins, wherein the urea, urease, source of calcium ions, and source of non-urease proteins are provided in effective amounts suitable to cause crystallization of calcium carbonate.

In various embodiments, the source of non-urease proteins comprises an enzyme stabilizer. In various embodiments, the enzyme stabilizer comprises nonfat milk powder. In various embodiments, the solution comprises about 4 grams/liter non-fat milk powder. In various embodiments, the source of calcium ions comprises calcium chloride dehydrate. In various embodiments, the solution comprises about 0.25 M to about 0.67 M calcium chloride. In various embodiments, the solution comprises about 0.37 M to about 1 M urea. In various embodiments, the solution comprises about 0.85 g/L to about 3 g/L urease. In various embodiments, the enzyme stabilizer comprises casein.

Methods of producing an EICP-treated soil are disclosed herein. The methods may comprise contacting a granular, cohesionless soil with a solution comprising, urea, urease, a source of calcium ions, and a source of non-urease proteins, wherein the EICP-treated soil comprises a carbonate content of less than about 3% weight by weight.

In various embodiments, the EICP-treated soil comprises a carbonate content of between about 3% weight by weight and about 0.5% weight by weight. In various embodiments, the EICP-treated soil comprises an unconfined compressive strength of about 0.5 MPa or more. In various embodiments, the EICP-treated soil comprises an unconfined compressive strength of between about 0.5 MPa and about 2 MPa. In various embodiments, the source of non-urease proteins comprises an enzyme stabilizer. In various embodiments, the enzyme stabilizer comprises nonfat milk powder. In various embodiments, the solution comprises 4 grams/liter non-fat milk powder. In various embodiments, the solution comprises about 0.25 M to about 0.67 M calcium chloride. In various embodiments, the solution comprises about 0.37 M to about 1 M urea. In various embodiments, the solution comprises about 0.85 g/L to about 3 g/L urease. In various embodiments, the enzyme stabilizer comprises casein.

BRIEF DESCRIPTION OF THE DRAWINGS

With reference to the following description and accompanying drawings.

DETAILED DESCRIPTION

Figure 1:
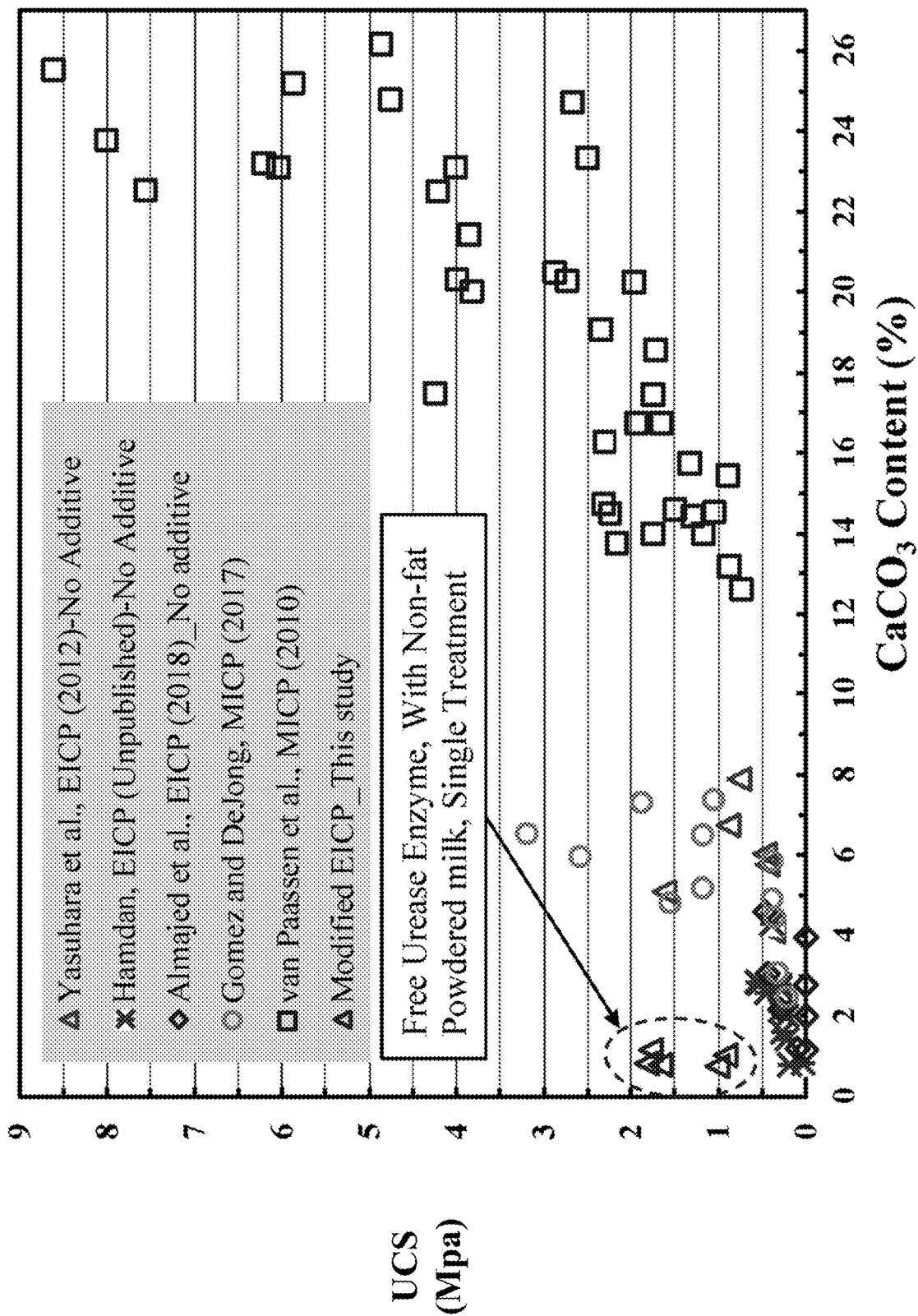
FIG. 1 illustrates the relative compressive strengths of samples treated with biocementation methods in accordance with various exemplary embodiments.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for energy dispersive x-ray analysis, x-ray diffraction, microbially-induced carbonate precipitation, compression testing, and/or the like may not be described in detail herein. As applicable, the connecting lines shown in various figures contained herein are intended to represent exemplary functional relationships and/or physical couplings between various elements. It should be noted that many alternative or additional functional relationships or physical connections may be present in a practical biocementation system, related methods, and/or products arising therefrom.

As used herein, "EICP" is used interchangeably with "enzyme induced carbonate precipitation" and refers to methods of carbonate precipitation via hydrolysis of urea (ureolysis) that use agriculturally-derived free urease enzyme as a source of urease. EICP occurs when, under certain environmental conditions (e.g., pH), the hydrolysis of urea leads to carbonate precipitation in the presence of divalent cations.

As used herein, "EICP-treated soil" means soil that has been treated with one or more of the methods disclosed herein.

As used herein, "carbonate precipitation" means mineral precipitation that may include one or more cations that may produce one of several phases of carbonate minerals, including but not limited to calcite. In a preferred embodiment, calcium carbonate precipitates form cementation bonds at inter-particle contacts in the starting material and fill in void spaces in the starting materials (thereby increasing the tendency of the starting material to dilate, or expand in volume, when sheared), and/or cementation of adjacent particles of the starting material.

As used herein, "purification fold" is determined by dividing the specific activity of an extract after a purification step by the specific activity of the crude extract (initial specific activity). Purification fold shows the efficiency of each purification step in removing non-protein cellular components and reducing the amounts of non-target proteins.

As used herein, "saturated" means that the soil has reached its maximum water content; if any more water is added it will either drain downward, flow upwards, or turn the soil into a suspension wherein there is little to no inter-particle contact.

As used herein, "specific urease activity" means specific activity obtained by dividing the urease activity by the total amount of protein (U/mg of protein). Specific activity is an indication of purity of an extract.

As used herein, "total units" refers to a measure of urease content in extracted solutions. Total units of urease enzyme in each extraction solution was calculated as urease activity multiplied by the volume of the solution. The total units of urease in a certain volume of extract represents how fast ammonia can be liberated by that volume of extract when the medium is saturated with urea (i.e., when the concentration of urea is twice the affinity constant value of the enzyme, km).

As used herein, "unit yield" means the total number of units in each extract divided by the initial mass of raw material used for extraction (i.e. urease content per gram of raw material, U/g of raw material). It represents the efficiency of the extraction process in terms of the amount of extracted enzyme.

As used herein, "urease activity" means the micromoles of ammonia liberated per minute by 1 ml (if liquid) or 1 g (if powder) of urease enzyme (i.e., U/g or U/ml).

Principles of the present disclosure contemplate the development of methods of biocementation for increasing the compression strength of treated granular soils. Exemplary embodiments disclose biocementation methods that may result in granular soils with improved mechanical strength, and/or that may utilize smaller quantities of reagents, and/or that may result in smaller quantities of undesirable byproducts such as ammonium chloride.

An exemplary method of biocementation is disclosed herein. In various embodiments, the method of biocementation comprises treating granular, cohesionless soil with enzyme induced carbonate precipitation. In various embodiments, the soil comprises sand. However, in various embodiments the soil may comprise one or more of sand, silt, soil, clay, sediments, sawdust, fractured crystalline rocks, cracked concrete and sedimentary rocks including but not limited to conglomerate, breccia, sandstone, siltstone, shale, limestone, gypsum, and dolostone.

In various embodiments, the soil is treated with a solution comprising urea, urease, a source of calcium ions, and a source of non-urease protein. In various embodiments, the source of calcium ions is calcium chloride dihydrate. However, the solution may comprise any source of calcium ions suitable for use in biocementation. In various embodiments, the source of non-urease protein comprises an enzyme stabilizer. In various embodiments, the source of non-urease protein may comprise an organic additive. In various embodiments, the source of non-urease protein comprises a dairy product. In various embodiments, the source of non-urease protein comprises a bovine dairy product. In various embodiments, the enzyme stabilizer comprises casein. In various embodiments, the enzyme stabilizer comprises non-fat milk powder.

In various embodiments, the source of non-urease proteins may comprise casein and/or whey. In various embodiments, the source of non-urease proteins may comprise accessory proteins associated with urease, having no urease activity themselves. In various embodiments, the source of non-urease proteins may jack bean. In various embodiments, the source of non-urease proteins may comprise an extract of jack beans. In various embodiments, the source of non-urease proteins may comprise one or more of jack bean, sword bean. jack bean meal, soybean, and watermelon seeds. However, the source of non-urease proteins may comprise any suitable source of proteins other than urease. In various embodiments, non-urease proteins may comprise one or more of canavalin, concanavalin, and canatoxin, However, the non-urease proteins may comprise any proteins other than urease suitable for use in methods of biocementation.

In various embodiments, the source of non-urease protein may increase the viscosity of the solution. Higher viscosity solution may improve conversion of precipitated calcium carbonate to calcite, thereby improving the strength and stability of EICP-treated soil. Higher viscosity solution may increase calcite formation at soil particle contact points relative to soil particle surfaces, thereby improving the strength and stability of EICP-treated soil.

In various embodiments, the non-urease proteins may interact with urease and/or affect the activity of urease so as to improve the growth and/or stability of calcite crystal formation. In various embodiments, the non-urease proteins may affect the solution so as to improve the growth and/or stability of calcite crystal formation.

In various embodiments, the enzyme stabilizer stabilizes urease and/or facilitates precipitation. The enzyme stabilizer may stabilize urease against environmental changes. Interaction between the enzyme stabilizer and calcium ions may provide nucleation points for carbonate precipitation. Interaction between the enzyme stabilizer and calcium ions may improve carbonate precipitation efficiency and/or yield. Interaction between casein and calcium ions may provide nucleation points for carbonate precipitation.

In various embodiments, the enzyme stabilizer lowers the rate of carbonate precipitation. The enzyme stabilizer may chelate calcium ions. Casein may chelate calcium ions. In various embodiments, chelation of calcium ions slows the rate of carbonate precipitation. A slowed rate of carbonate precipitation may be beneficial to the morphology and/or crystal growth of the precipitate. A slowed rate of carbonate precipitation may delay the onset of bio-clogging, in which a decrease in the permeability of EICP-treated soil is caused by precipitation of carbonate and deposition into soil voids. A slowed rate of carbonate precipitation may facilitate disbursement of the solution in the EICP-treated soil.

The relatively large calcite crystals precipitated in the specimens treated with the EICP solutions containing an enzyme stabilizer may be due to the slower rate of precipitation. Molecular interactions between urease enzyme and milk proteins may reduce the accessibility of active sites on the enzyme to urea and consequently lower the precipitation rate, consistent with the findings of Bachmeier et al. Casein in the milk may also act as a chelating agent reducing the precipitation rate. In addition, casein may precipitate and provide nucleation sites that favor calcite crystal formation and growth.

In various embodiments, the biocementation solution comprises about 0.67 M calcium ions (wherein about mean +/−0.2 M). In various embodiments, the biocementation solution comprises about 0.25 M calcium ions (wherein about mean +/−0.2 M). However, the biocementation solution may comprise any suitable concentration of calcium ions.

In various embodiments, the biocementation solution comprises about 1.0 M urea. In various embodiments, the biocementation solution comprises about 0.37 M urea (wherein about mean +/−0.2 M). However, the biocementation solution may comprise any suitable urea concentration.

In various embodiments, the biocementation solution comprises about 3 grams/liter urease having activity of about 3500 U/g. In various embodiments, the biocementation solution comprises about 0.85 grams/liter (wherein about mean +/−0.5 g/L). However, the biocementation solution may comprise any suitable urease concentration at any suitable activity level.

In various embodiments, the biocementation solution comprises 4 grams/liter non-fat milk powder. However, the biocementation solution may comprise any suitable enzyme stabilizer concentration.

In various embodiments of the present disclosure, a method of producing an EICP-treated soil is described. The method of producing an EICP-treated soil may comprise contacting a granular, cohesionless soil with a solution comprising urea, urease, a source of calcium ions, and a source of non-urease proteins, as described herein.

In various embodiments, the resulting EICP-treated soil comprises a carbonate content of less than about 3% weight by weight (wherein about means +/−0.5% w/w) and an unconfined compressive strength of at least about 0.5 MPa (wherein about means +/−0.1 MPa). In various embodiments, the resulting EICP-treated soil comprises a carbonate content of between about 3% weight by weight (wherein about means +/−0.5% w/w) and about 0.5% weight by weight (wherein about means +/−0.1% w/w). In various embodiments, the resulting EICP-treated soil comprises an unconfined compressive strength of between about 2 MPa (wherein about means +/−0.5 MPa) and about 0.5 MPa (wherein about means +/−0.1 MPa). In various embodiments, the resulting EICP-treated soil comprises a carbonate content of less than about 0.5% weight by weight (wherein about means +/−0.1% w/w) and an unconfined compressive strength of at least about 2 MPa (wherein about means +/−0.5 MPa).

The disclosed method may result in a higher strength EICP-treated soil with only a single treatment of solution. The disclosed method may result in lower concentrations of precipitated carbonate in the EICP-treated soil. Benefits of the disclosed method may include production of an EICP-treated soil using lower concentrations of substrate and enzyme, for example, urea and urease, respectively. Benefits of the disclosed method may include decreased production of undesirably byproduct, for example, ammonium, during production of the EICP-treated soil. Benefits of the disclosed method may include cheaper, more technically feasible, and/or more environmentally friendly EICP-treated soil production.

Example 1

EICP Treatment Solution. EICP treatment solutions were prepared by dissolving calcium chloride dihydrate ($CaCl_2 \cdot 2H_2O$), urea, urease enzyme (with activity of ≈3500 U/g), and, in some cases, non-fat milk powder into 18.2 MG deionized (DI) water. Three different EICP treatment solutions were employed for soil treatment. Solution 1, referred to as the baseline EICP solution, was composed of 1.0 M urea, 0.67 M calcium chloride, and 3 g/l enzyme. These concentrations were selected based on our previous study. Solution 2, referred to as the modified EICP solution, was composed of 1.0 M urea, 0.67 M calcium chloride, 3 g/l enzyme, and 4 g/l non-fat milk powder. Solution 3, referred to as the low concentration modified EICP solution, was composed of 0.37 M urea, 0.25 M calcium chloride, 0.85 g/l enzyme, and 4 g/l non-fat milk powder.

Soil Treatment. Ottawa 20/30 sand (mean grain size of 0.6 mm; maximum void ratio, $e_{max}$, =0.742; minimum void ratio, $e_{min}$, =0.502; specific gravity of solids, $G_s$, =2.65; 99% $SiO_2$) was treated with the three different EICP solutions. Two specimens were prepared using Solution 1, three specimens were prepared using Solution 2, and two specimens were prepared using Solution 3. Test specimens were prepared by thoroughly mixing 350 g of sand with 75 ml (about one pore volume) of the EICP solution and then immediately placing the mixture into a 5.08 cm-(2 inch-) diameter acrylic column in three lifts. Each lift of sand was then gently tamped so that the sand in the cylinder reached a final height of 10.16 cm (4 inches) above the base, corresponding to a relative density of 76%. Following densification of the sand by tamping, the treatment solution was always a few millimeters above the soil surface, indicating that the packed soil was in a near saturated condition. The top of each column was closed with aluminum foil in order to minimize loss of solution by evaporation. Each column was allowed to cure at room temperature (approximately 20° C.) for 3 days. After the curing, the specimens were rinsed with about one pore volume of DI water and then oven-dried at 40° C. until no change in mass was observed. The dried specimens were subject to unconfined compression strength testing at a constant axial strain rate of 1.27 mm/minute.

Carbonate Content Measurement. Gravimetric acid digestion was employed to measure the carbonate content of a portion of each specimen following unconfined compression testing. About 80-100 g of each specimen was soaked into 4 M hydrochloric acid solution. The soaked specimen was then rinsed and dried. The mass difference before and after the acid digestion was considered to be the mass of calcium carbonate precipitated in the specimen. Mass of the precipitate over the mass of sand after digestion is reported as the carbonate content in each specimen.

Microscale Identifications. X-Ray Diffraction (XRD) analysis was performed on intact pieces of selected specimens to identify the mineral crystal phases in each sample. The samples were ground using an agate mortar and pestle and powdered onto a standard glass slide for XRD analysis. Scanning electron microscopy (SEM) imaging was also performed on intact cemented chunks of material to visualize the morphology of the precipitates and the precipitation pattern in the soil. Energy dispersive X-ray (EDX) analysis was carried out in conjunction with SEM imaging to determine the elemental composition of the precipitates within each sample. The samples were coated with carbon prior to SEM/EDX analysis.

The results of soil treatment in terms of unconfined compressive strength and carbonate content for specimens treated using the three different solutions are presented in Table 1.

TABLE 1

UCS results and carbonate content in the specimens treated with different solutions.

| EICP Solution | Test No. | Peak Strength (MPa) | $CaCO_3$ (%) |
| --- | --- | --- | --- |
| Solution 1 | 1 | .133 | 1.63 |
| | 2 | .158 | 0.58 |
| Solution 2 | 1 | 1.817 | 0.82 |
| | 2 | 1.654 | 0.79 |
| | 3 | 1.763 | 1.17 |
| Solution 3 | 1 | 1.000 | 0.57 |
| | 2 | 1.396 | 0.71 |

Comparing the unconfined compressive strength of the specimens treated using the baseline solution (Solution 1, no powdered milk) to the modified EICP solution (Solution 2, with powdered milk), adding powdered milk to the EICP solution resulted in unconfined compressive strength between 1.654 MPa and 1.817 MPa for the three specimens treated with the modified EICP solution while the specimens treated with the EICP solution that did not contain powdered milk had unconfined compressive strengths of 0.133 MPa and 0.158 MPa at similar carbonate content. The dramatic increase in strength for the specimens treated with the modified EICP solution was unexpected.

Comparing the specimens treated with Solution 2 (the modified EICP solution) to those treated with Solution 3 (the low concentration modified EICP solution), lowering the concentration of urea and calcium chloride by 62.5% (from 1.0 M urea and 0.67 M $CaCl_2$ to 0.37 M urea and 0.25 M $CaCl_2$)) and the concentration of enzyme by about 72% (from 3 g/l to 0.85 g/l) led to a reduction of approximately 30% in the unconfined compressive strength. The average unconfined compressive strength decreased from approximately 1.7 MPa for the three specimens treated with the modified EICP solution to an average unconfined compressive strength of approximately 1.2 MPa for the specimens treated with the low concentration modified EICP solution. The unconfined compressive strength of the specimens treated with the low-concentration modified EICP solution (Solution 3, which contained powdered milk) was an order of magnitude greater than the unconfined compressive strength of the specimens treated with the higher concentration solution that did not contain powdered milk (Solution 1, the baseline solution).

The theoretical maximum carbonate content was approximately 1.4% for the specimens treated with Solutions 1 and 2 (the higher concentration solution) and was about 0.5% for the specimens treated with Solution 3 (the lower concentration solution). For the two specimens treated with Solution 1, the measured carbonate content was approximately 59% less and 16% more than the theoretical maximum. For the three specimens treated with Solution 2, the measured carbonate content was approximately 41% less, 44% less, and 16% less than the theoretical maximum. For the two specimens treated with Solution 3, the measured carbonate content was approximately 14% more and 42% more than the theoretical maximum. Variations in carbonate content may be attributed to non-uniform distribution of the precipitate within each specimen, as only a portion of each specimen was used for acid digestion. Loss of precipitates suspended in the pores or loosely attached to the particles due to rinsing at the end of the treatment process may result in a measured carbonate content less than the amount of carbonate precipitated from the treatment solution.

Figure 2:
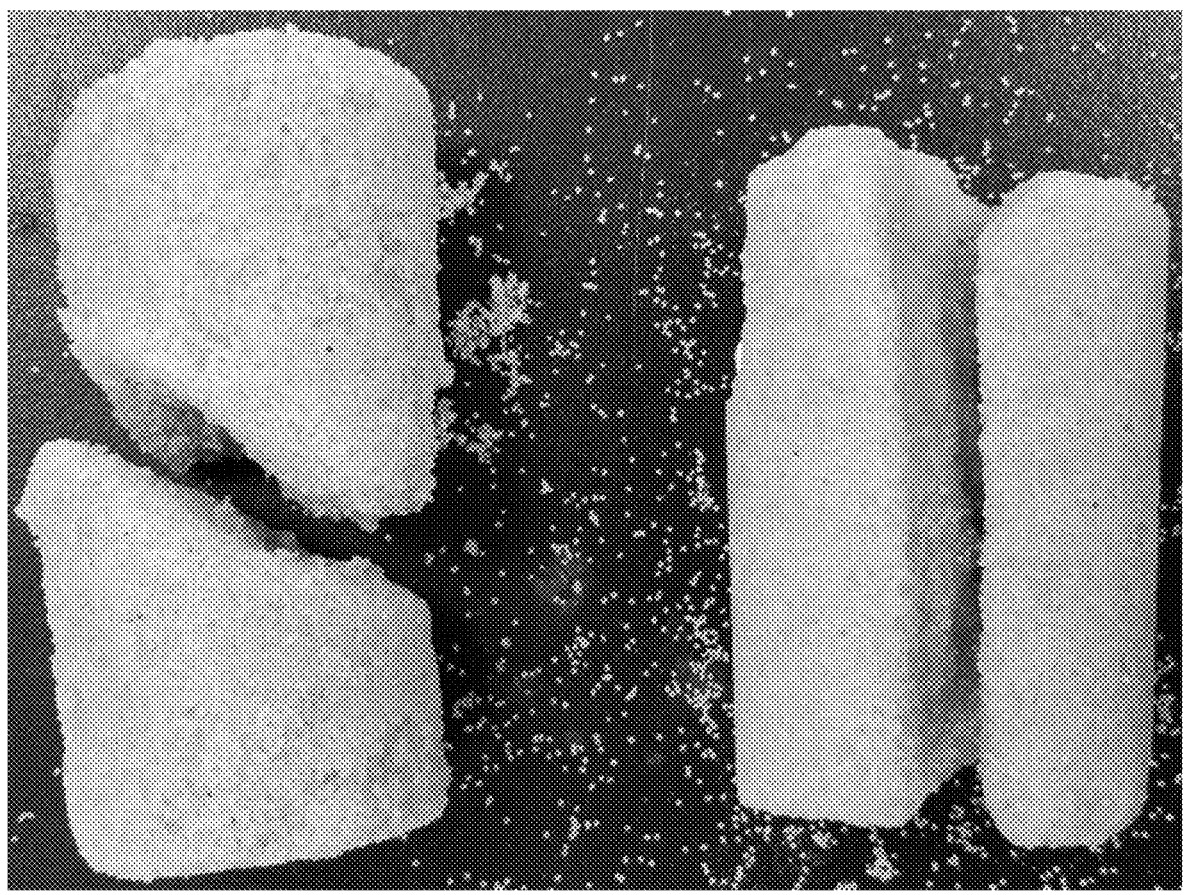
FIG. 2 depicts compression failure patterns of samples treated with biocementation methods in accordance with various exemplary embodiments.
Figure 3A:
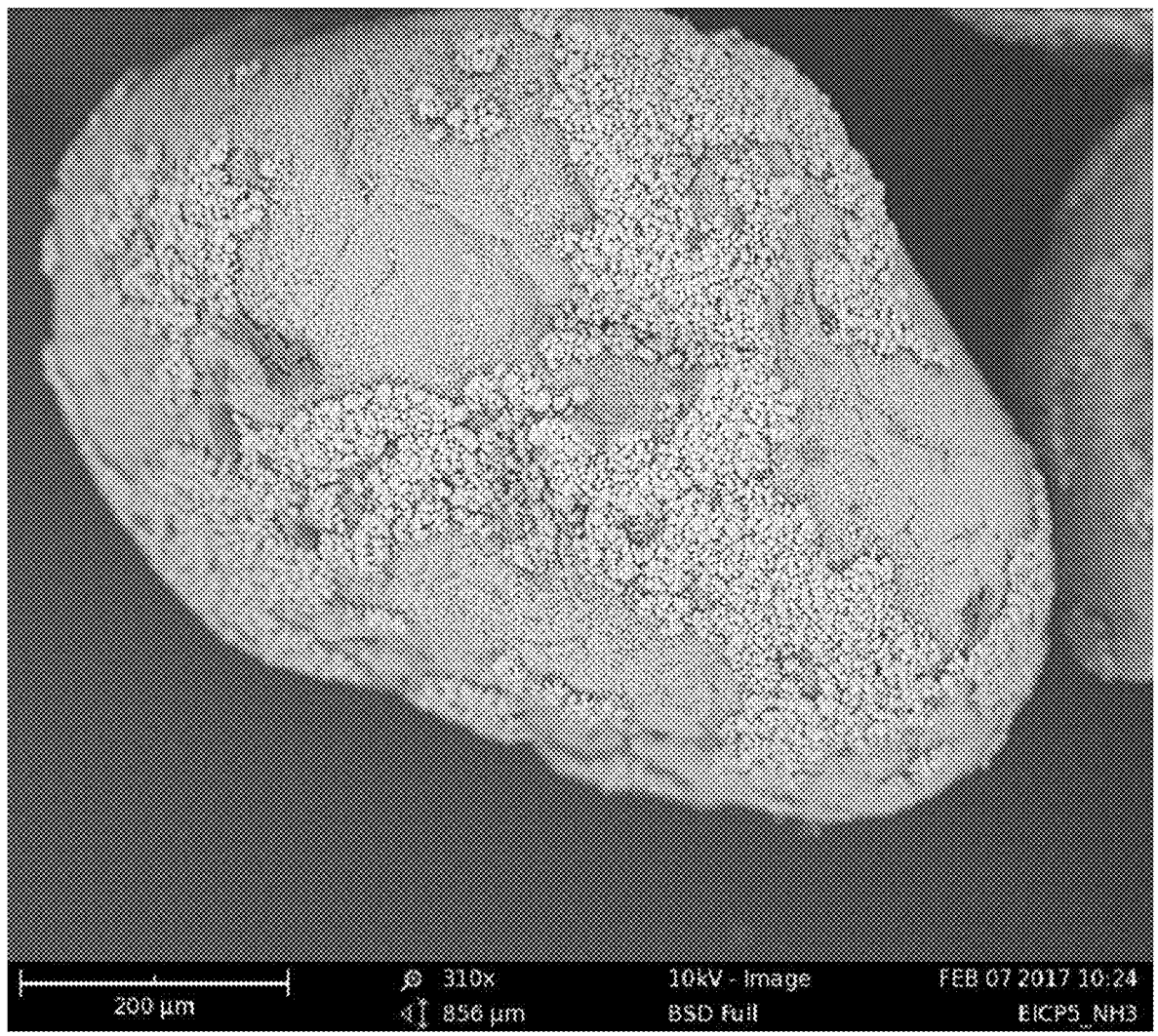
FIGS. 3a and 3b depict scanning electron microscope images of sample particles treated using biocementation methods that result in relatively small calcite crystals.
Figure 3B:
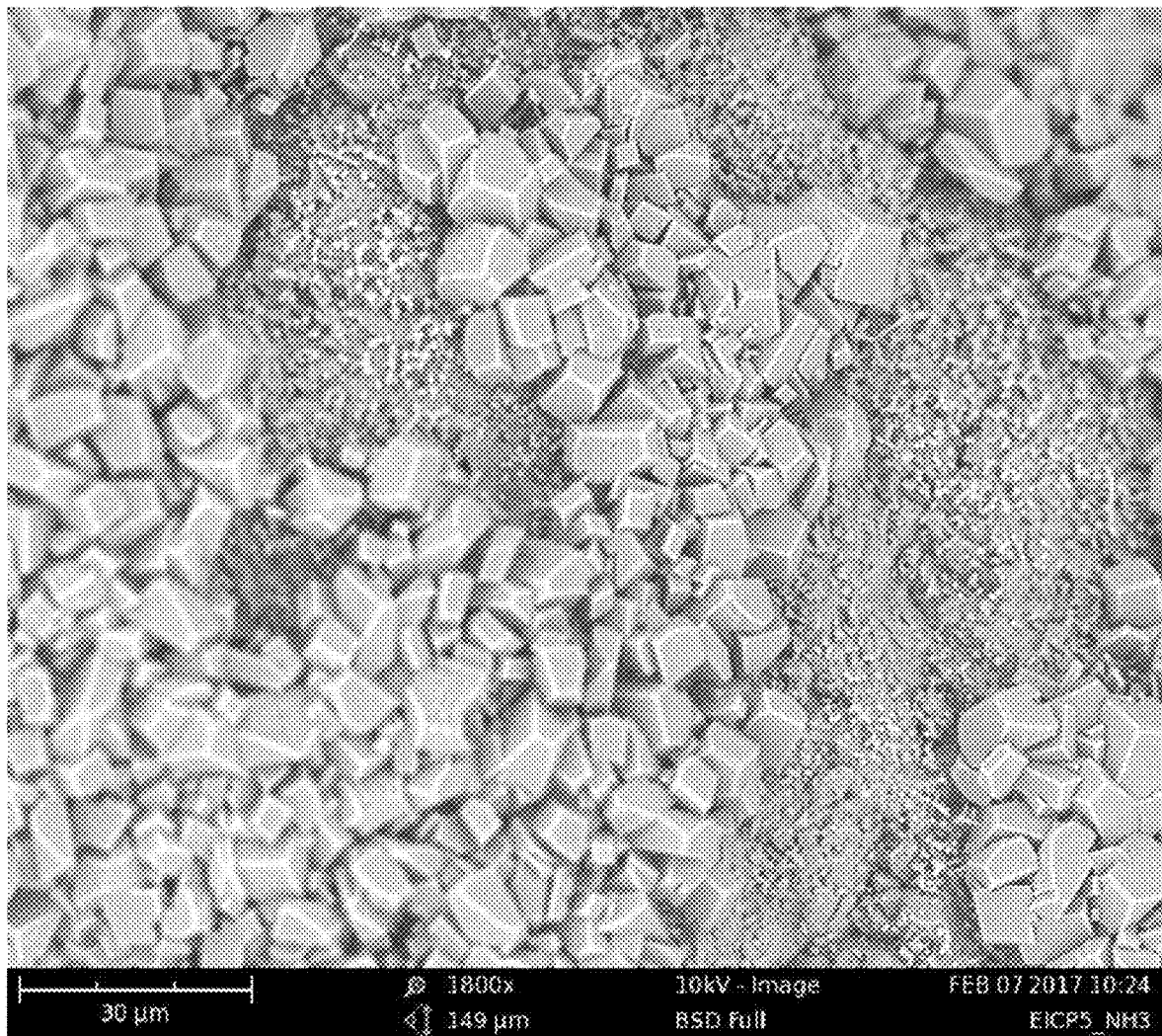
Figure 3C:
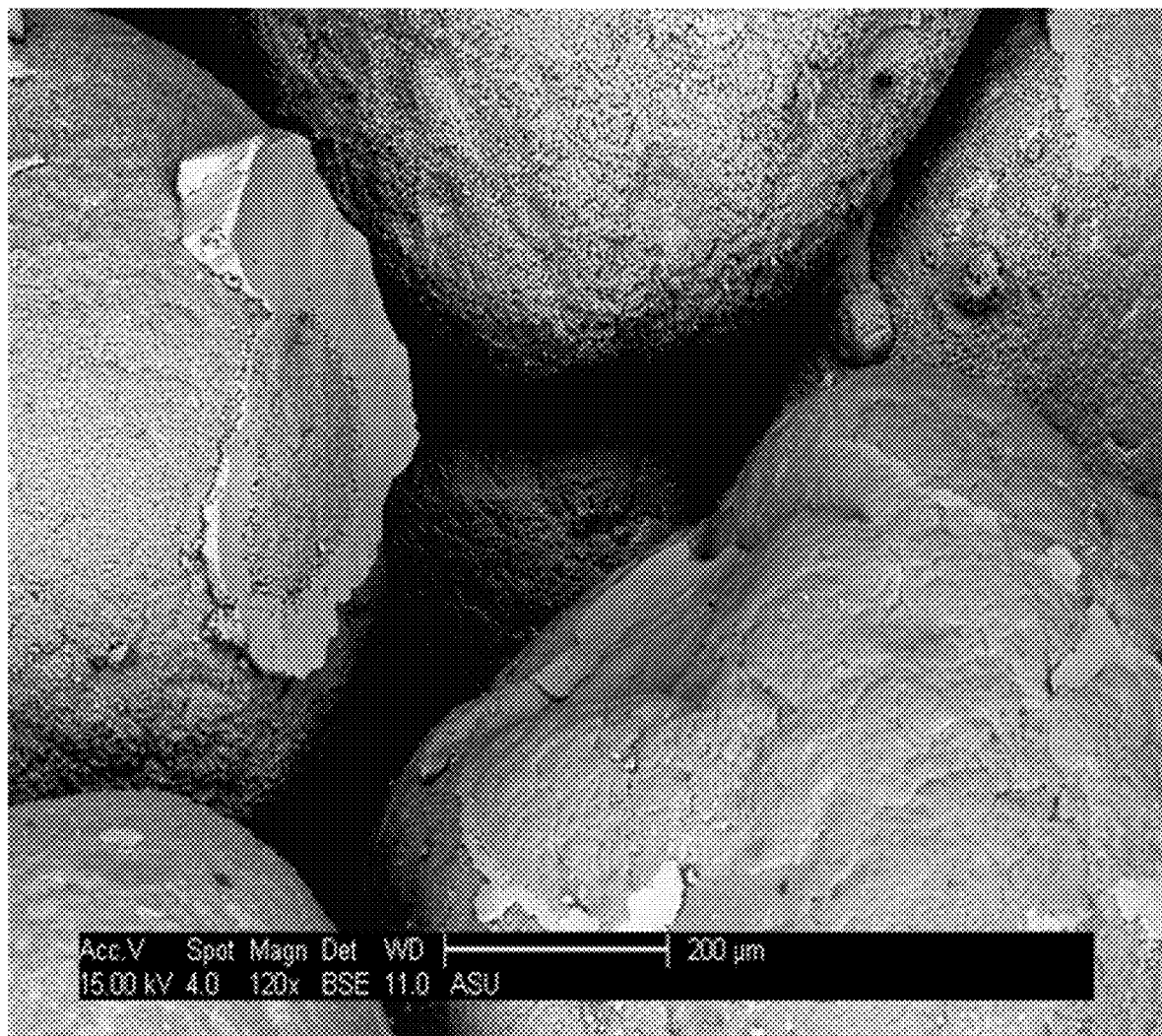
FIGS. 3c and 3d depict scanning electron microscope images of sample particles treated using biocementation methods, in accordance with various exemplary embodiments, that result in relatively large calcite crystals formed at inter-particle contacts.
Figure 3D:
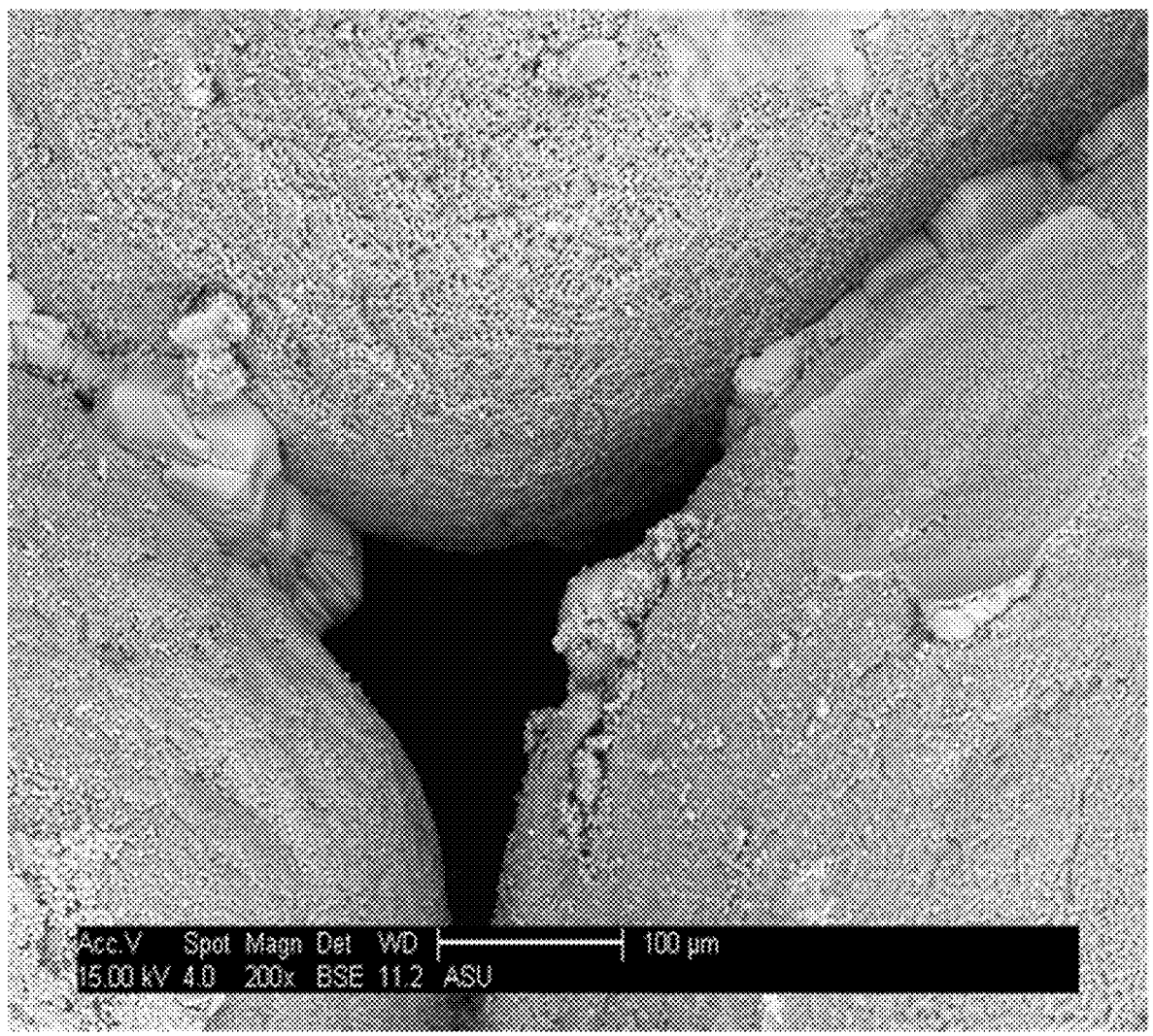
Figure 4A:
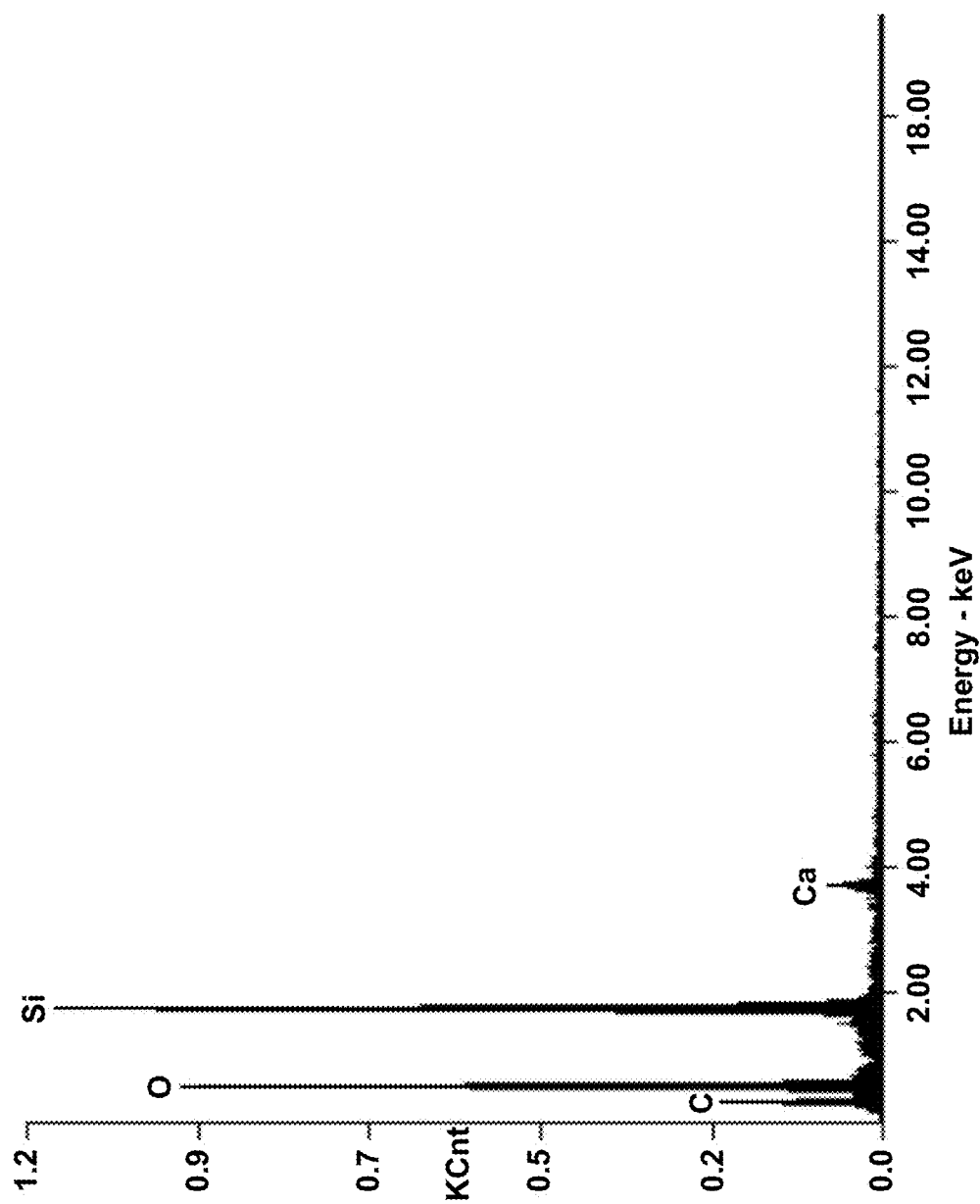
FIG. 4a illustrates the results of energy dispersive x-ray analysis on rhombohedral calcite crystals located at an interparticle contact that evidence the presence of calcium carbonate and silica, in accordance with various exemplary embodiments.
Figure 4B:
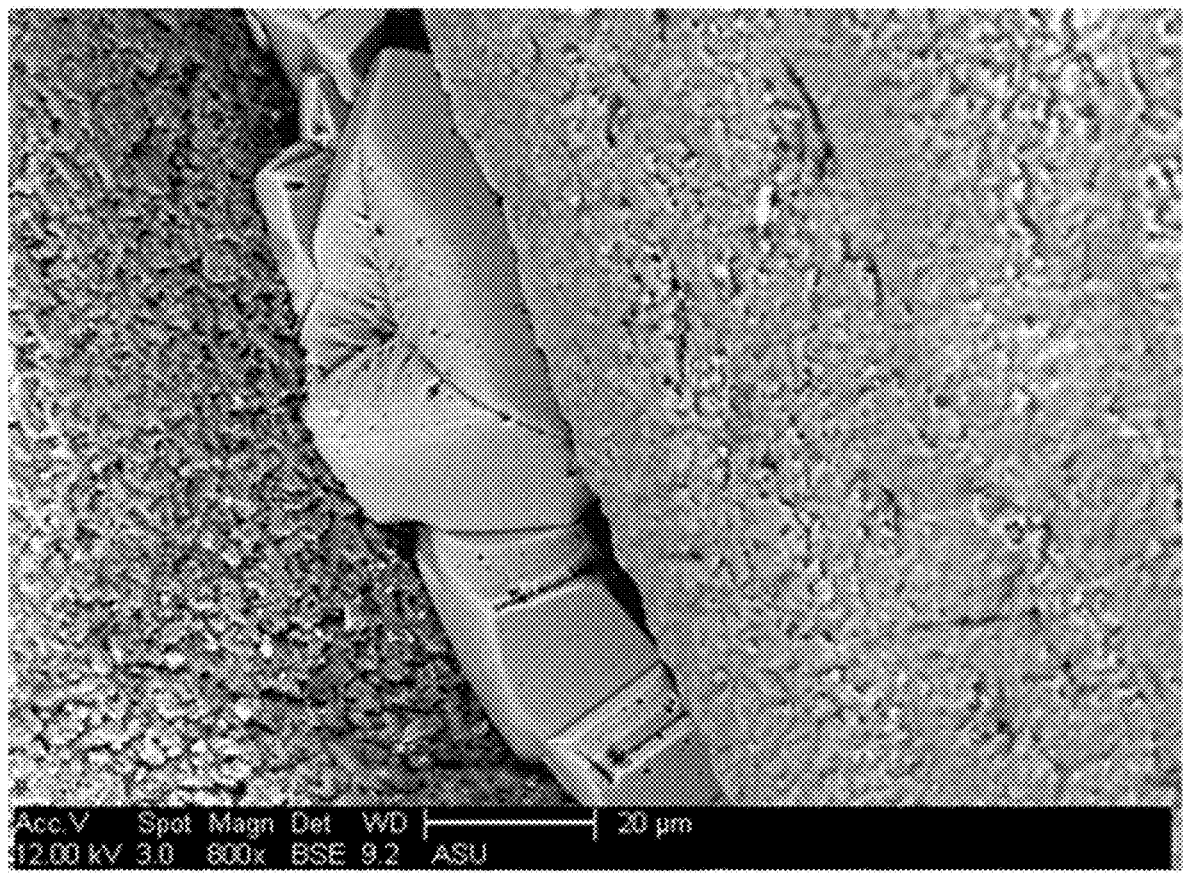
FIG. 4b depicts a scanning electron microscope image of rhombohedral calcite crystals located at an interparticle contact, in accordance with various exemplary embodiments.
Figure 4C:
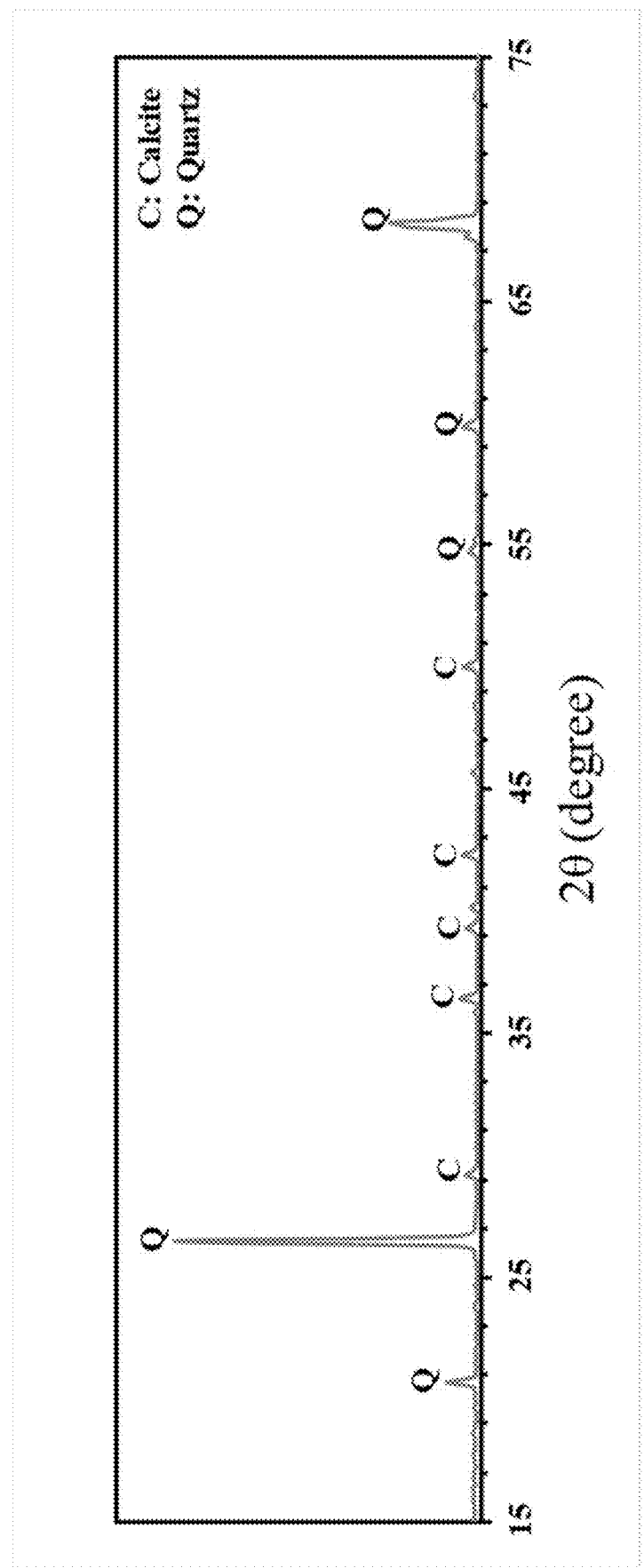
FIG. 4c illustrates the x-ray diffraction spectrum of rhombohedral calcite crystals located at an interparticle contact showing peaks corresponding to a calcite crystal phase and quartz sand, in accordance with various exemplary embodiments.

Observations of the failure pattern of the specimens following unconfined compressive loading indicated that the specimens treated using the Solution 2 and Solution 3 failed by tensile splitting whereas the specimens treated with the Solution 1 failed in shear. FIG. 2 shows the different failure pattern of the Specimen 1 (shear failure) and Specimen 2 (tensile splitting failure). SEM images, presented in FIGS. 3a-3d, show a difference in precipitation patterns between the specimens treated with and without milk in the EICP treatment solution. For the specimens treated using the solution that did not contain powdered milk, the precipitated carbonate may form relatively small crystals distributed over the surface of the sand particle. When powdered milk was added into EICP solution, relatively large calcite crystals may form, with precipitation focused mainly at inter-particle contacts. The pattern of precipitation may contribute to the increase strength of the specimens prepared with an EICP solution containing powdered milk compared to specimens treated with an EICP solution that did not contain powdered milk. The results of EDX and XRD testing, presented in FIGS. 4a-4c, together confirmed precipitation of calcium carbonate in the calcite phase.

Figure 5:
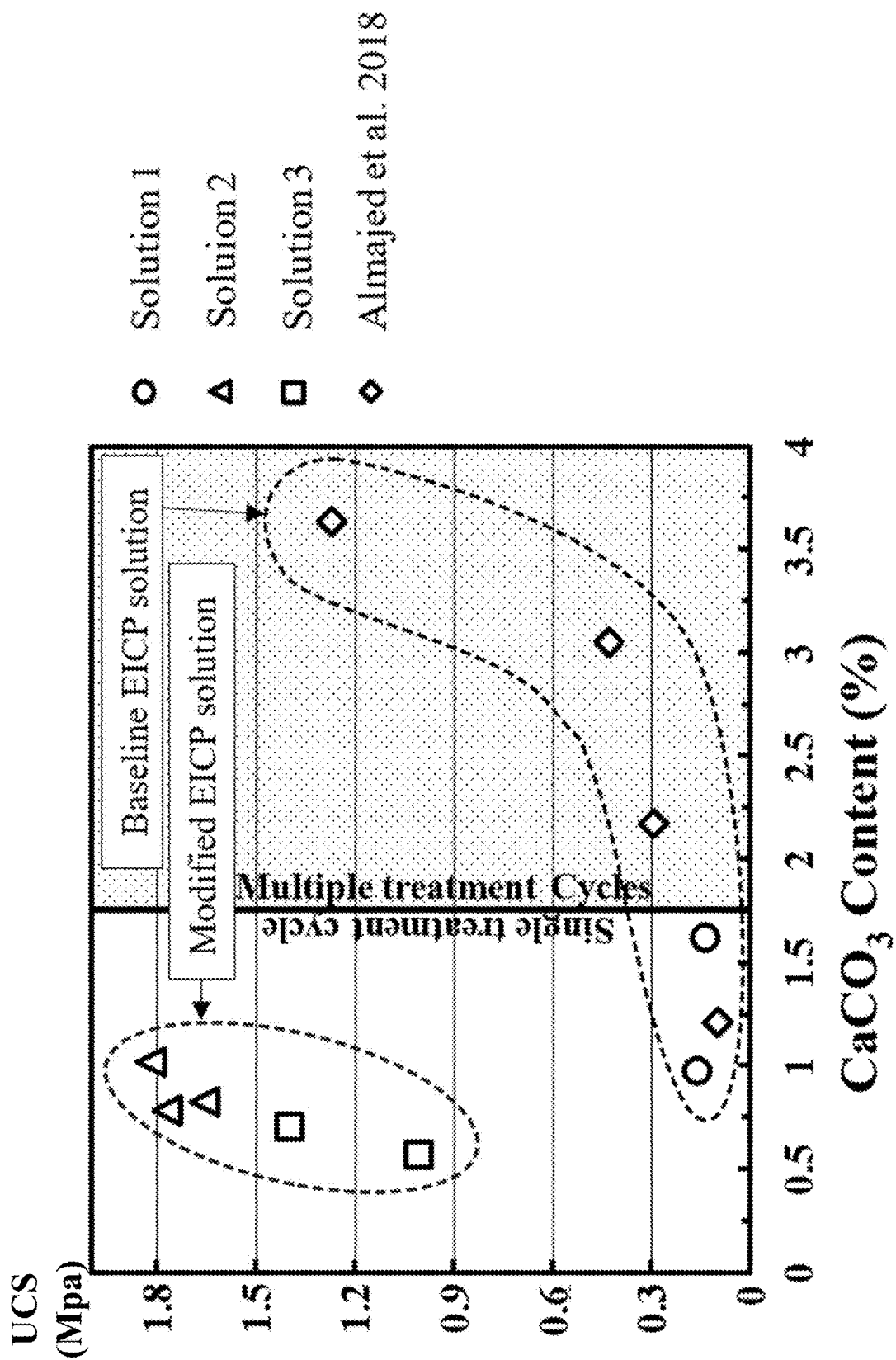
FIG. 5 illustrates unconfined compressive strength versus calcium carbonate content for samples treated with various biocementation methods in accordance with various exemplary embodiments.

The surprising unconfined compressive strength data from the tests reported herein wherein powdered milk was used in the treatment solution are included on FIG. 1 and are presented in closer detail in FIG. 5. FIG. 1 shows the relationship between precipitated calcium carbonate ($CaCO_3$) content and unconfined compressive strength for soil treated via MICP and EICP based upon values reported in the literature. Except for samples treated with the biocementation method disclosed herein, a carbonate content in excess of 3% (w/w) and multiple cycles of treatment were required to achieve an unconfined compression strength in excess of 0.5 MPa. FIG. 5 also includes the results of tests reported by Almajed el al. on soils treated using treatment Solution 1 (the solution without powdered milk) in which specimens were subject to multiple cycles of treatment to generate carbonate contents greater than 2%.

The unconfined compressive strength of soils improved by carbonate precipitation may depend not only on the amount of precipitated carbonate but also on the pattern of precipitation. Relatively high strength may be achieved at relatively low carbonate content with treatment by a biocementation solution comprising urea, urease, calcium ions, and an enzyme stabilizer. The significant advantages of the high strength at low carbonate content achieved by adding powdered milk to the EICP treatment solution may include reductions in the concentration of substrate and enzyme required to achieve a target compressive strength, reduction in production of the undesirable ammonium chloride by-product generated by the hydrolysis of urea, and reduction in the number of cycles and duration of treatment required to achieve a desired strength.

Additional principles of the present disclosure are contained in Appendices attached to, and filed with, U.S. Provisional Application No. 62/729,221 filed on Sep. 10, 2018, the contents of which are hereby incorporated by reference in their entirety.

Example 2

Urease enzyme extraction from various organic sources is described herein.

Urease enzyme from sword jack beans (*Canavalia gladiata*, Sheffield's Seed), jack bean meal (*Canavalia enformis*, Spectrum Chemical), soybeans (Glycine mar, Laura Soybeans), and sugar baby watermelon seeds (*Citrullus lanatus*, Johnnyseeds) was obtained via three stages of chemical extraction. The sword jack beans and watermelon seeds were dehusked prior to extraction (husk comprises approximately 67% of the mass of watermelon seeds and 14% of the mass of jack beans). In the first stage of enzyme extraction, 50 g of each species was soaked in 200 ml of an extraction solution overnight at pH 7.5 and 4° C. The extraction solution consisted of 20 mM phosphate buffer and 2 mM ethylenediaminetetraacetic acid (EDTA). The solutions containing beans or seeds were then homogenized in a kitchen blender for around 2 minutes to disrupt the cells and tissues for enzyme extraction. Since the jack bean meal was in powder form, the solution containing jack bean meal was homogenized by stirring with a glass rod. Each homogenized mixture was passed through kitchen cheesecloth fabric to separate coarse solids from the enzyme-containing solution. To remove finer insoluble matter, the filtrate was centrifuged for 15 minutes at 21500 g. Excess fat in the supernatant from centrifugation was removed by passing the supernatant through glass wool. The solution obtained in this manner is referred to herein as the crude extract.

In the second stage of enzyme extraction, referred to herein as the first fractionation step, acetone fractionation was used to precipitate (i.e. salt-out) urease proteins from the crude extract. Forty six percent (46%) (v/v) pre-chilled acetone (i.e., acetone at −20° C.) was slowly added to the crude extract while it was being stirred in an ice chamber. The mixture was then centrifuged at between 0° C. and 4° C. at 25000 g for 15 min and the supernatant was discarded. The remaining pellet was suspended in 40 ml of extraction buffer. After letting the suspension stand at 4° C. overnight, the suspension was stirred for 2 hours and centrifuged again at 25000 g between 0° C. and 4° C. for 15 minutes. The supernatant collected following the second centrifugation was the yield of this first fractionation step.

In the third stage of enzyme extraction, referred to herein as the second fractionation step, the extract was further purified using acetone fractionation. In this second fractionation step, the supernatant solution obtained from the previous step was diluted 1:1 with extraction buffer. Next, 25% (v/v) pre-chilled acetone was gently added to the diluted solution and the mixture was immediately centrifuged for 10 min at 21500 g. Finally, 40% (v/v) pre-chilled acetone was added to the supernatant from this centrifugation step and the mixture was centrifuged once again at between 0° C. and 4° C. for 15 min at 25000 g. The pellet from this final centrifugation step was suspended in 20 ml of extraction buffer as the yield of the second fractionation step.

The necessity of using a pH buffer solution and a chelating agent in crude extraction process for jack bean was also assessed in this study. For this purpose, the extraction solution (i.e., the phosphate buffer and EDTA) was replaced with 18.2 MΩ deionized (DI) water for the initial (first stage) crude extraction from the jack beans.

A summary of the results of the activity assessments for the extractions from each plant source is 370 presented in Table 2.

four plant sources: jack bean (JB), jack bean meal (JBM), soybean (SB), and watermelon seed (WS). A band in the SDS-PAGE results appears at around 90 kDa in all of the extraction solutions and in the commercial enzymes used as control. Urease protein from plants and fungi are reported to have molecular weights of around 90 kDa.

TABLE 2

| Plant Species | Product | Volume of Extraction | Total Units U | Total Protein mg | Specific Activity U/mg of protein | Fold Pure | Loss of Enzyme % |
|---|---|---|---|---|---|---|---|
| Dehusked jack bean | Crude in extraction solution | 130 | 168064 | 5495 | 31 | 1 | 0 |
| | 1st acetone fractionation | 41 | 101710 | 2191 | 46 | 1.48 | 39.5 |
| | 2nd acetone fractionation | 20 | 55873 | 476 | 117 | 3.77 | 66.8 |
| | Crude in water | 126 | 152250 | 5632 | 27 | 1 | 0 |
| Jack bean meal | Crude in extraction solution | 93 | 94634 | 4008 | 24 | 1 | 0 |
| | 1st acetone fractionation | 48 | 39974 | 2167 | 18 | 0.75 | 57.8 |
| | 2nd acetone fractionation | 20 | 19691 | 810 | 24 | 1 | 79.2 |
| Soybean | Crude in extraction solution | 95 | 17093 | 4683 | 4 | 1 | 0 |
| | 1st acetone fractionation | 44 | 12806 | 1598 | 8 | 2 | 25.1 |
| | 2nd acetone fractionation | 21 | 3212 | 427 | 8 | 2 | 81.2 |
| Dehusked watermelon seed | Crude in extraction solution | 133 | 20407 | 2013 | 10 | 1 | 0 |
| | 1st acetone fractionation | 56 | 13581 | 609 | 22 | 2.2 | 33.4 |
| | 2nd acetone fractionation | 20 | 6143 | 104 | 59 | 5.9 | 69.9 |

Figure 6:
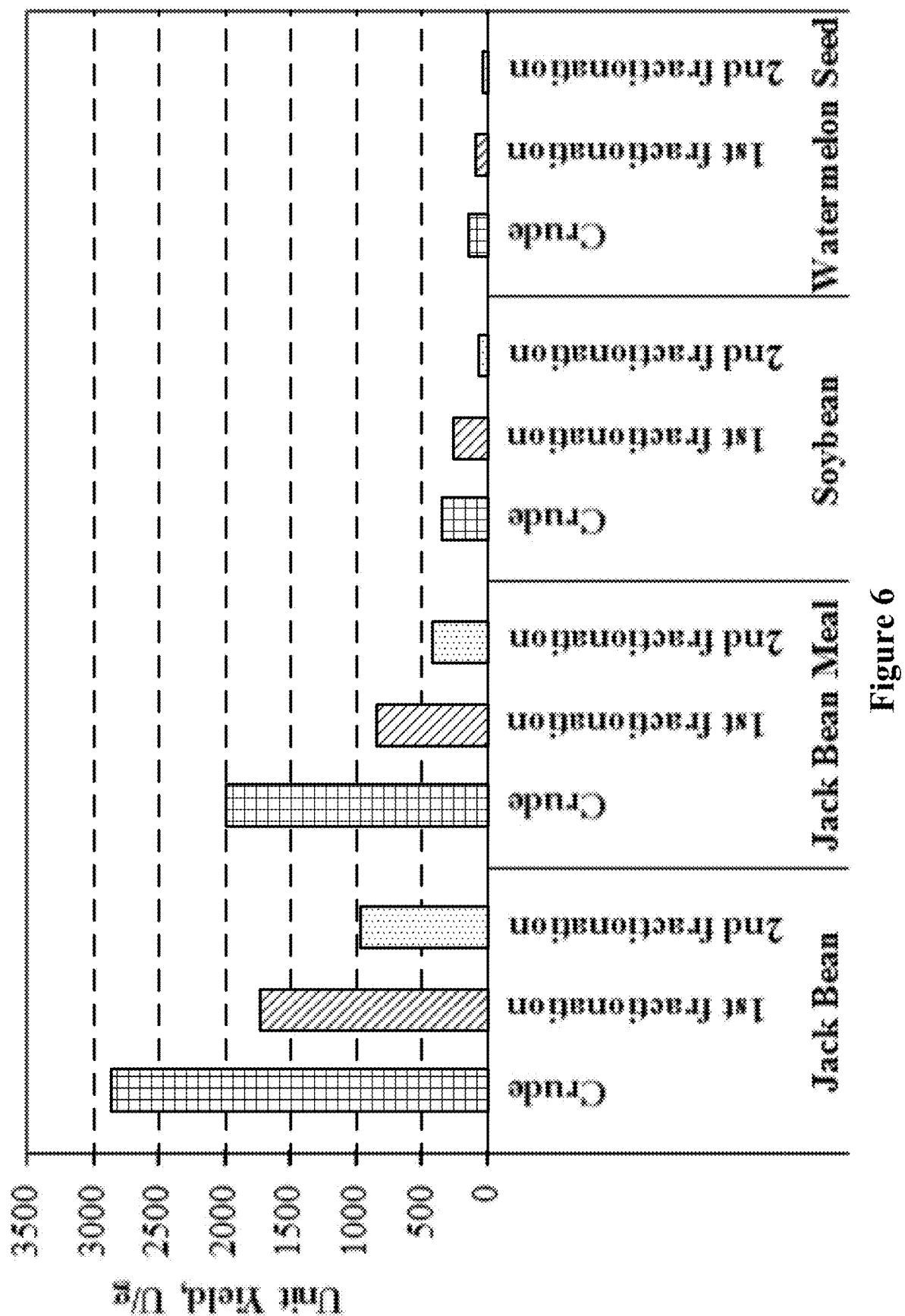
FIG. 6 illustrates urease yield at various points of extraction in accordance with various exemplary embodiments.

The two steps of the purification process (i.e., the first and second fractionation steps) resulted in 2.2-fold and 5.9-fold purification for watermelon seed and 1.5-fold and 3.8-fold purification for jack bean for the two fractionation steps, respectively. The crude extraction from jack bean in DI water resulted in a similar number of total units as the extraction in the phosphate buffer and EDTA solution. The urease proteins in jack bean crude extract may remain stable in DI water without adding pH buffer solution and a chelating agent. FIG. 6 compares the unit yield for each plant source after each extraction and purification step. The lower amount of enzyme units and specific activity of jack bean meal compared to jack bean may be attributed to the process used to create the meal. Heating and grinding methods utilized to produce jack bean meal may result in loss of some urease content.

Example 3

Determination of urease protein purification levels, concentration levels, and activity are described herein.

Figure 7:
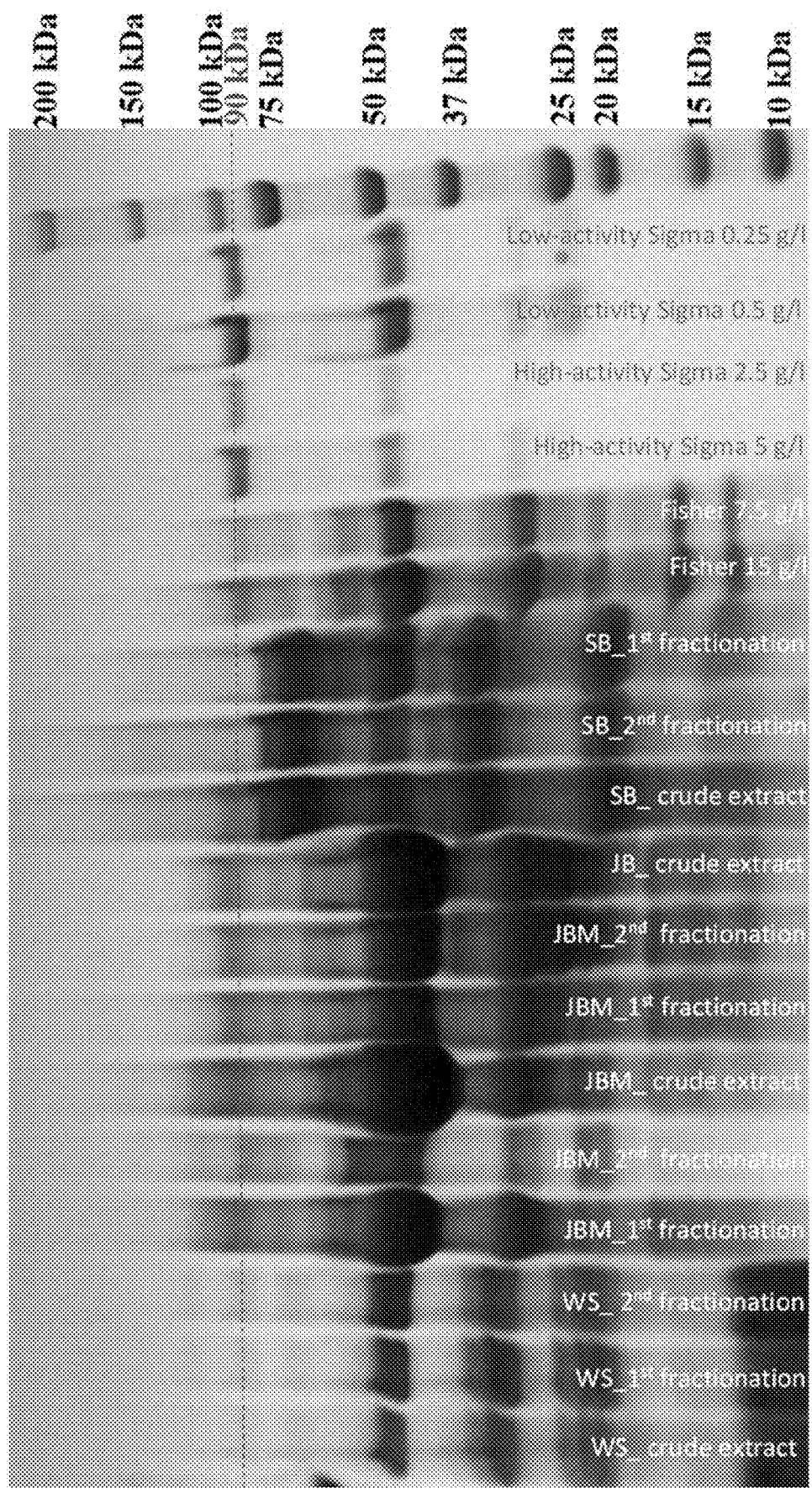
FIG. 7 illustrates SDS-PAGE analysis of urease extract activity in accordance with various exemplary embodiments.

SDS-PAGE (sodium dodecyl sulfate polyacrylamide gel electrophoresis), which separates proteins based on their molecular weight, was employed to quantify the level of purification and verify the presence of urease protein in the crude extract and in the yield from each fractionation step. Three commercial jack bean urease enzymes, referred to herein as high-activity Sigma Aldrich enzyme (U1500, Type III, powder, 42700 U/g activity, Sigma Aldrich), low-activity Sigma Aldrich enzyme (U1875, Type III, supplied in glycerol solution, 800 U/ml activity, Sigma Aldrich) and Fisher Scientific enzyme (U2125, powder, no activity reported on the label, Fisher Scientific), were used as control. In this method, the extracts were first diluted, mixed with 4×SDS-PAGE 217 loading dye containing 25% beta-mercaptoethanol, and heated at 95° C. for 10 minutes. The samples were then loaded on 12% SDS-PAGE resolving gel which was stained with Coomassie blue to express the proteins. The gel was electrophoresed at a constant voltage of 200 V for 35 220 min. FIG. 7 illustrates the presence of urease enzyme in the crude extraction solutions from the The Bradford protein assay method was applied to determine the protein concentration in each extraction solution and the commercial enzymes. A commercial protein assay kit (RC DC protein assay kit II, 5000122, Bio-Rad) was used for this purpose. In this colorimetric method, Coomassie blue attaches to protein molecules and creates a blue solution. The color intensity of the solution measured using a spectrophotometer at a wavelength of 595 nm was translated to protein concentration using a standard calibration curve.

Figure 8A:
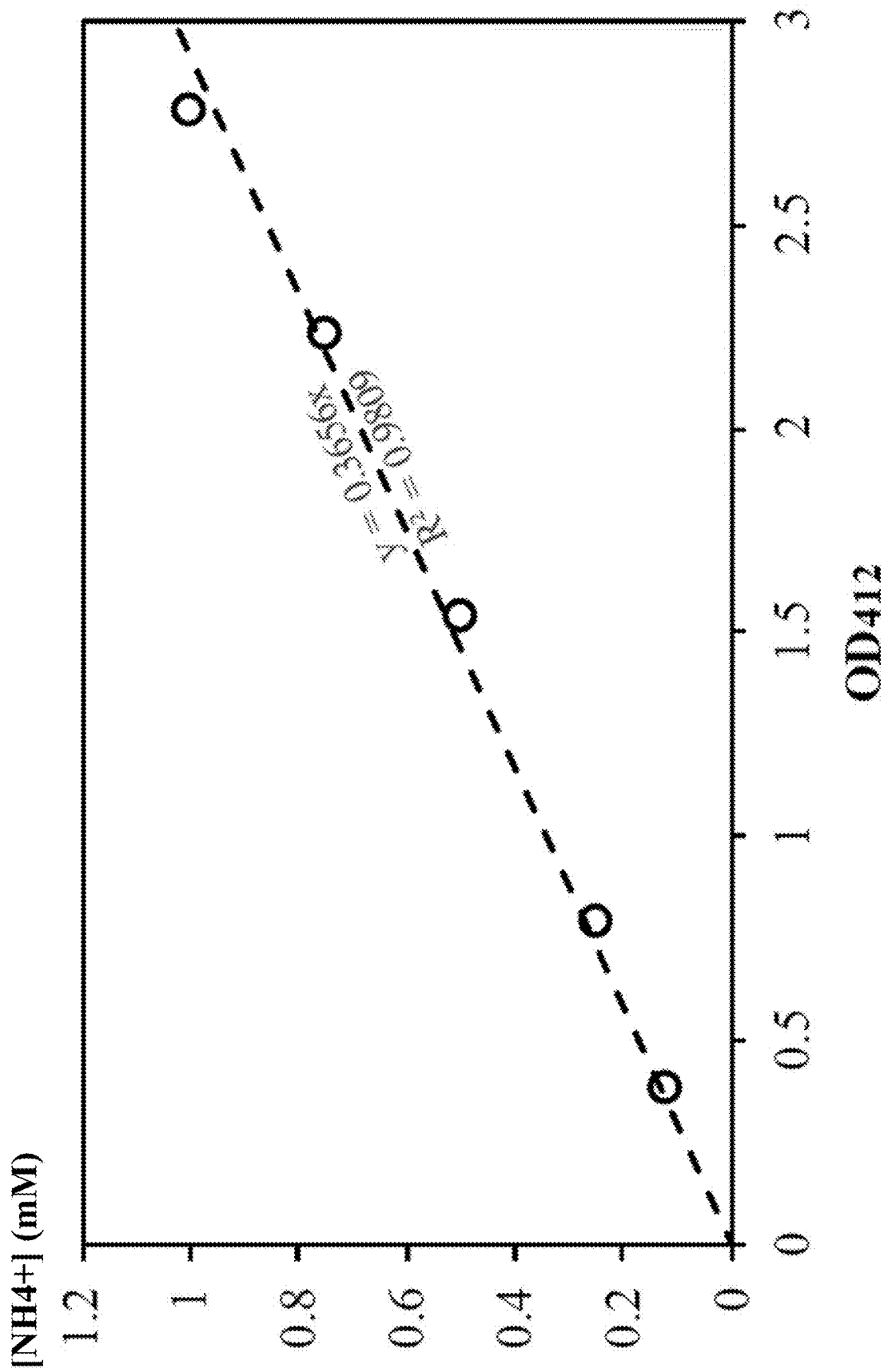
FIG. 8a illustrates a calibration curve used for measurement of urease activity.

To measure the urease activity of the crude extract and the yield from each fractionation step, 0.3 ml of the urease solution was added to 9.7 ml of urea and phosphate buffer solution (pH 7.5) in three 50 ml serum bottles. The concentrations of the urea and phosphate buffer in each bottle were 150 mM and 1 M, respectively. After adding the enzyme solution into each bottle, the bottle was immediately sealed using a stopper and aluminum seal and was gently shaken until the reaction was stopped by adding 5 ml of 10% trichloroacetic acid. The acid was added into the first bottle after 3 minutes, the second bottle after 5 minutes, and the third bottle after 10 minutes. Adding trichloroacetic acid causes precipitation and denaturation of urease protein. It also causes the ammonia gas generated from the solution to be returned into the solution as ammonium ions. After stopping the reaction, each bottle was opened, and the solution was diluted 100-fold using DI water. Then, 2 ml of the diluted solution was added to a cuvette containing 100 μl Nessler's reagent. The cuvette was placed in a spectrophotometer to measure the optical density of the solution at a wavelength of 412 nm (i.e. OD412). The concentration of ammonium liberated in the solution as a result of urea hydrolysis was determined using a calibration curve relating ammonium concentration to OD412. FIG. 8a illustrates the calibration curve utilized. Afterwards, for each enzyme solution, the ammonium concentration was plotted versus time and the decay function in Equation 7 was fitted to each data set.

Equation 7: $Y = a \cdot (1 - b \cdot e^{-cx})$, where a, b, and c are the Asymptote, Scale, and Decay rate of the reaction, respectively.

Figure 8B:
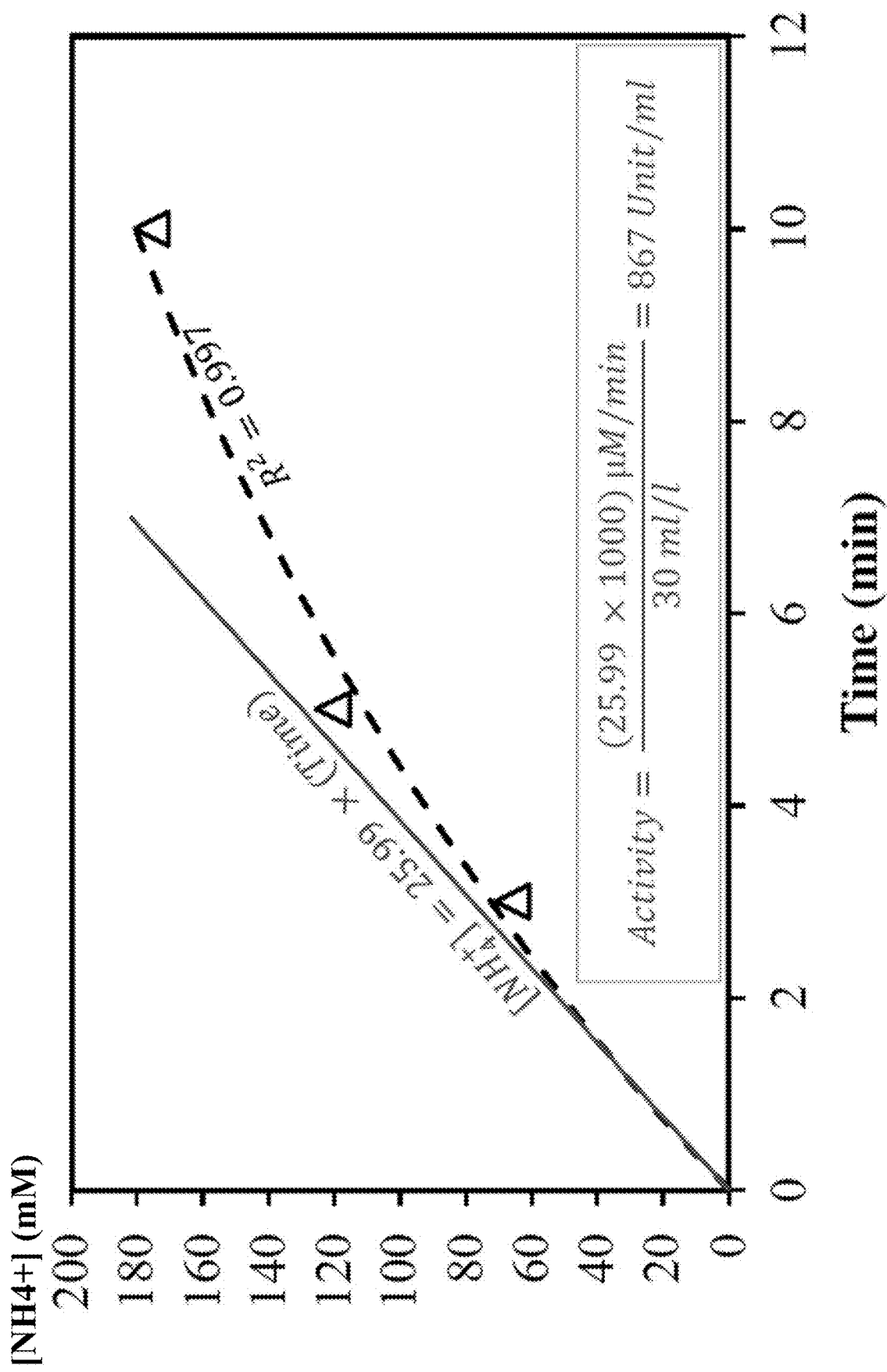
FIG. 8b illustrates urease activity of low-activity Sigma Aldrich enzyme in accordance with various exemplary embodiments.

The enzyme activity of the solution was calculated by dividing the slope of the initial linear part of the ammonium-time curve by enzyme concentration, as illustrated in FIG. 8b. To validate this activity measurement method, the activity of the low-activity Sigma Aldrich enzyme with a manufacturer-reported activity of 800 U/ml was measured. The activity of the Fisher Scientific enzyme (which does not have any activity value reported on the label) was also measured using this method for documentation purposes.

Example 4

Ionic composition of enzyme solutions is described herein.

As the crude extract from the dehusked jack bean had the highest unit yield, the crude jack bean extract was selected as the choice for further study and comparison with the commercial enzymes. Ion chromatography (IC) analysis was conducted to identify ions in the jack bean crude extract and the three commercial enzymes in solution. Concentrations of PO43−, NO3−, SO42−, NO2−, and chloride (Cl—) anions, and sodium (Na+), ammonium (NH4+), K+, Ca2+, and Mg2+ cations were measured using ion chromatography (Dionex ICS 5000+). The anion analysis was conducted using potassium hydroxide eluent at a 15 mM starting concentration, on a Dionex AS18 column at 59 mA suppressor output. Cation analysis was conducted using 20 mM methanesulfonic acid eluent starting concentration, on a Dionex CS12A column at 112 mA suppressor output. The calibration curves used for ion chromatography focused on PO43− and NO3— measurements, where PO43− values ranged from 0.05 mg/L to 5 mg/L and NO3− values ranged from 0.5 to 30 mg/L. Check standards were added every 10 samples, and 10% of all samples were spiked with 1 mg/L PO43− to verify peak locations.

Peaks were analyzed using the Chromeleon peak analysis software. The crude extract was tested without any dilution. Fisher Scientific and high-activity Sigma Aldrich enzymes, which are in powder form, were first dissolved in DI water at a concentration of 15 g/l, and then diluted by 1000 times (i.e. enzyme concentration of 15 mg/l). Low-activity Sigma Aldrich enzyme, which is dissolved in glycerol solution, was diluted by 500 times. All the samples were filtered using a 0.45 μm syringe filter prior to IC analysis. Table 3 illustrates the ionic compositions of various urease extracts and/or sources.

TABLE 3

|  | Crude Extract in Water mg/ml | Fisher Scientific mg/g | Sigma Aldrich_high activity mg/g | Sigma Aldrich low activity mg/ml |
| --- | --- | --- | --- | --- |
| F− | 0.000 | 96.100 | 81.400 | 0.580 |
| Cl− | 0.000 | 0.000 | 0.000 | 4.830 |
| NO2− | 0.000 | 0.000 | 0.000 | 0.000 |
| Br− | 0.048 | 31.940 | 31.973 | 0.253 |
| NO3− | 0.065 | 36.040 | 38.107 | 0.246 |
| SO4²− | 0.179 | 62.173 | 56.213 | 0.411 |
| PO4³− | 0.106 | 0.000 | 510.400 | 1.330 |
| Li+ | 0.000 | 0.000 | 0.000 | 0.000 |
| Na+ | 0.071 | 37.573 | 38.593 | 3.470 |
| NH4+ | 0.000 | 0.000 | 0.000 | 0.000 |
| K+ | 0.356 | 90.293 | 349.780 | 0.736 |
| Mg²+ | 0.727 | 31.260 | 30.833 | 0.232 |
| Ca+ | 0.215 | 123.020 | 119.267 | 0.870 |

Example 5

Correlation between non-urease protein content and EICP-treated soil was demonstrated as described herein.

EICP-treated soil specimens were evaluated for carbonate content, strength, morphology, kinetics, and mass with tube tests. Five EICP solutions were generated using various sources of urease, namely, crude urease extract in extraction solution, cruse urease extract in water, and three commercial urease enzymes (Fisher Scientific urease, High activity Sigma Aldrich urease, and Low activity Sigma Aldrich urease, respectively).

The compositions of the EICP solutions were the same except for the five different sources of urease enzyme. Each 50 ml test tube contained 50 ml of EICP treatment solution that consisted of 1.0 M urea, 0.67 M CaCl2-dihydrate, 4 g/l non-fat milk powder, and around 13,000 Units of free urease enzyme per liter. The number of urease enzyme units was fixed across all five solutions (approx. 13,000 units); however, the total protein concentration of each of the five solutions varied based on the source, purity, and/or extraction method of urease. Table 4 illustrates the protein concentration of various urease extracts and/or sources.

TABLE 4

|  | Crude Extract in Extraction Solution | Crude Extract in Water | Fisher Scientific | Sigma Aldrich_ High activity | Sigma Aldrich_ Low activity |
| --- | --- | --- | --- | --- | --- |
| Protein mg/g or mg/ml | 42.2 | 44.7 | 198.7 | 132.2 | 1.1 |
| Specific Activity U/mg of protein | 31 | 27 | 21 | 323 | 814 |

Therefore, the relative differences in protein concentrations of the five solutions are due to the presence non-urease proteins.

Each tube was placed on a shaker at 100 rpm and room temperature (22° C.±2° C.) for 96 hours. 100 μl samples were taken from each tube after 1, 2, 4, 16, 24, 48, and 72 hours, immediately diluted by 1000 times, and stored at 0-4° C. Afterwards, the diluted samples were analyzed via ion chromatography to determine the concentration of dissolved (unconsumed) calcium ions in the solution, from which the approximate rate of precipitation in each solution can be estimated. The pH of the reaction solution in each tube was also measured after 1, 16, 24, 48, and 72 hours. At the end of the test, each tube was centrifuged at 1500 rpm for 10 minutes and the supernatant was discarded. The remaining precipitates were rinsed twice by adding 30 ml DI water. After each rinsing, supernatant was removed via centrifugation at 1500 rpm for 10 minutes. Finally, the precipitates were dried at 40° C. until constant mass achieved. The mass of precipitates in each tube was measured by subtracting the mass of each empty tube from the mass of the tube after the final centrifugation step. Microscale identification analysis to characterize precipitate morphology (e.g., scanning electron microscopy and energy dispersive x-ray spectroscopy) was conducted on the precipitates.

Figure 9:
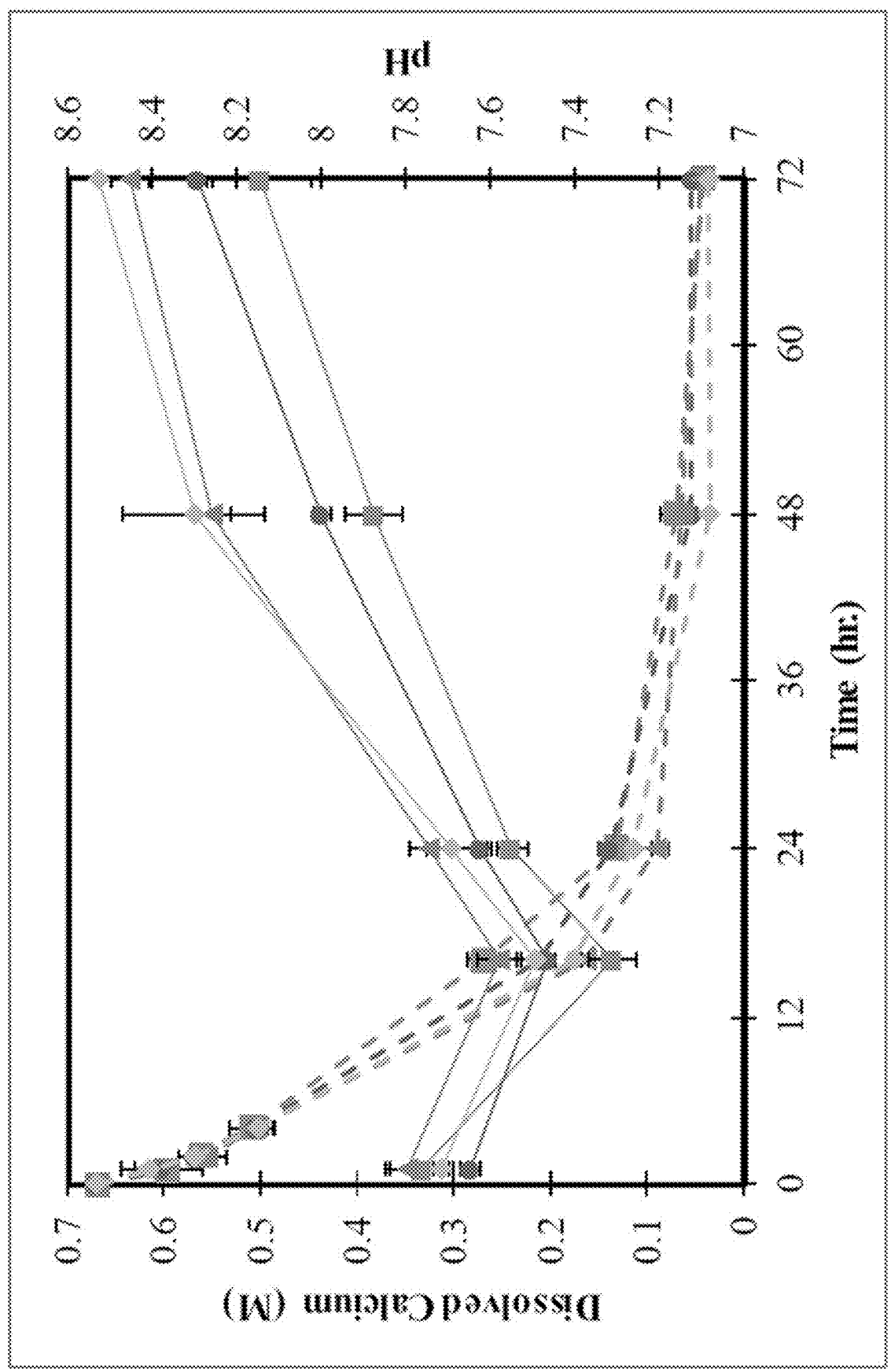
FIG. 9 illustrates dissolved calcium and pH of EICP solution over time in accordance with various exemplary embodiments.
Figure 10A:
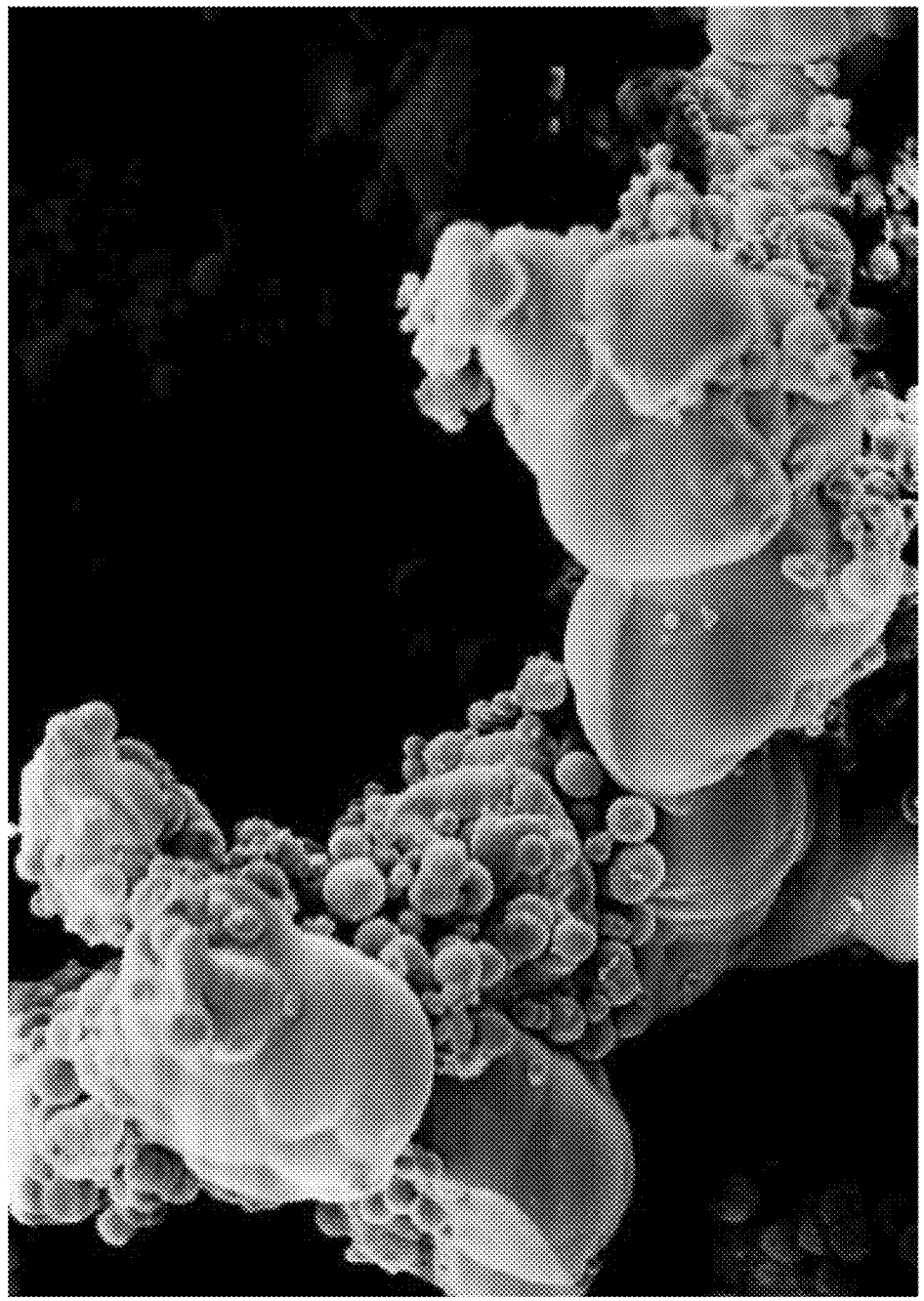
FIG. 10a through 10e illustrate SEM images of precipitates in tubes containing (a) crude extract, (b) Fisher Scientific enzyme, (c) high-activity Sigma Aldrich enzyme, and (d) low-activity Sigma Aldrich 506 enzyme; and (e) XRD spectra of the precipitates from each tube in accordance with various exemplary embodiments.
Figure 10B:
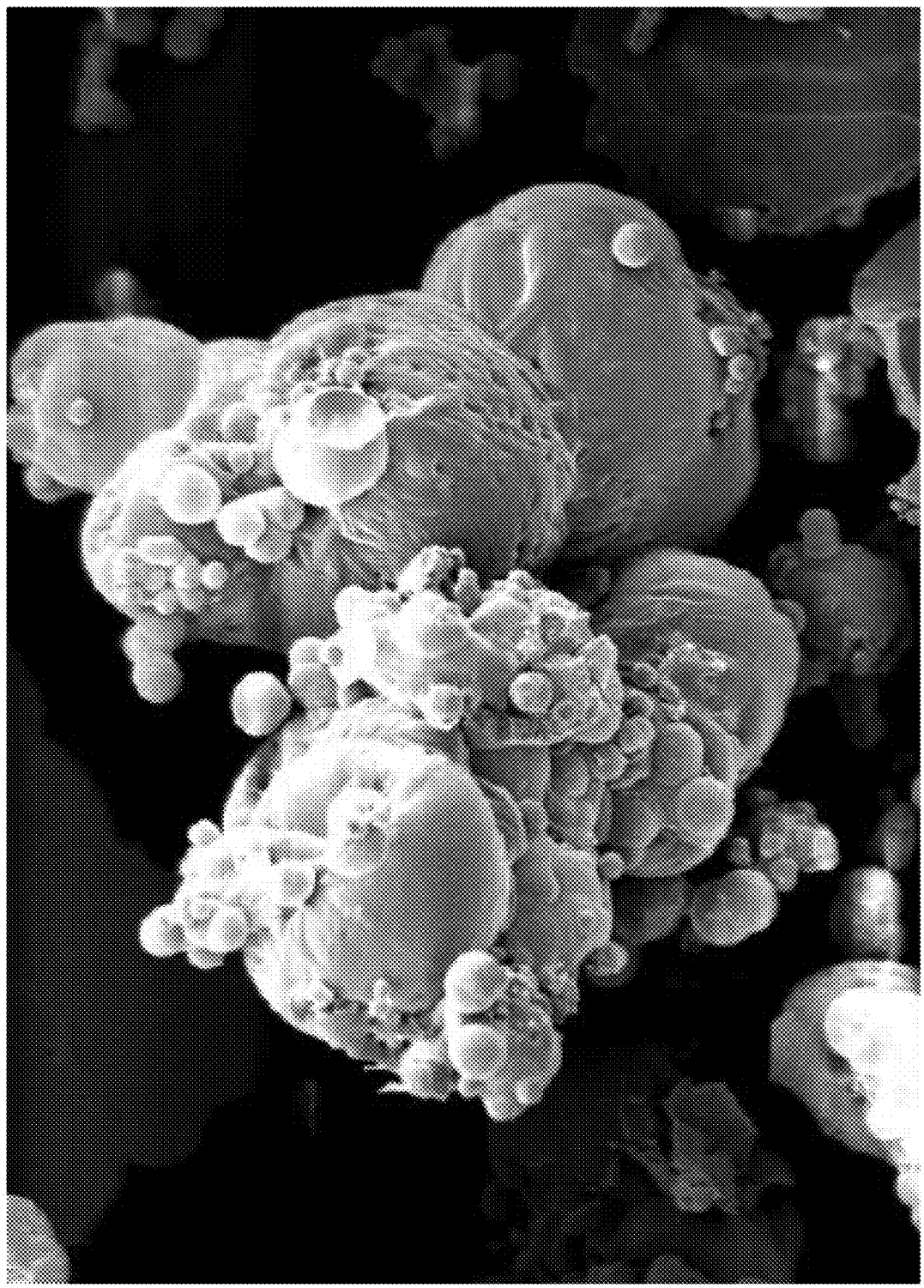
Figure 10C:
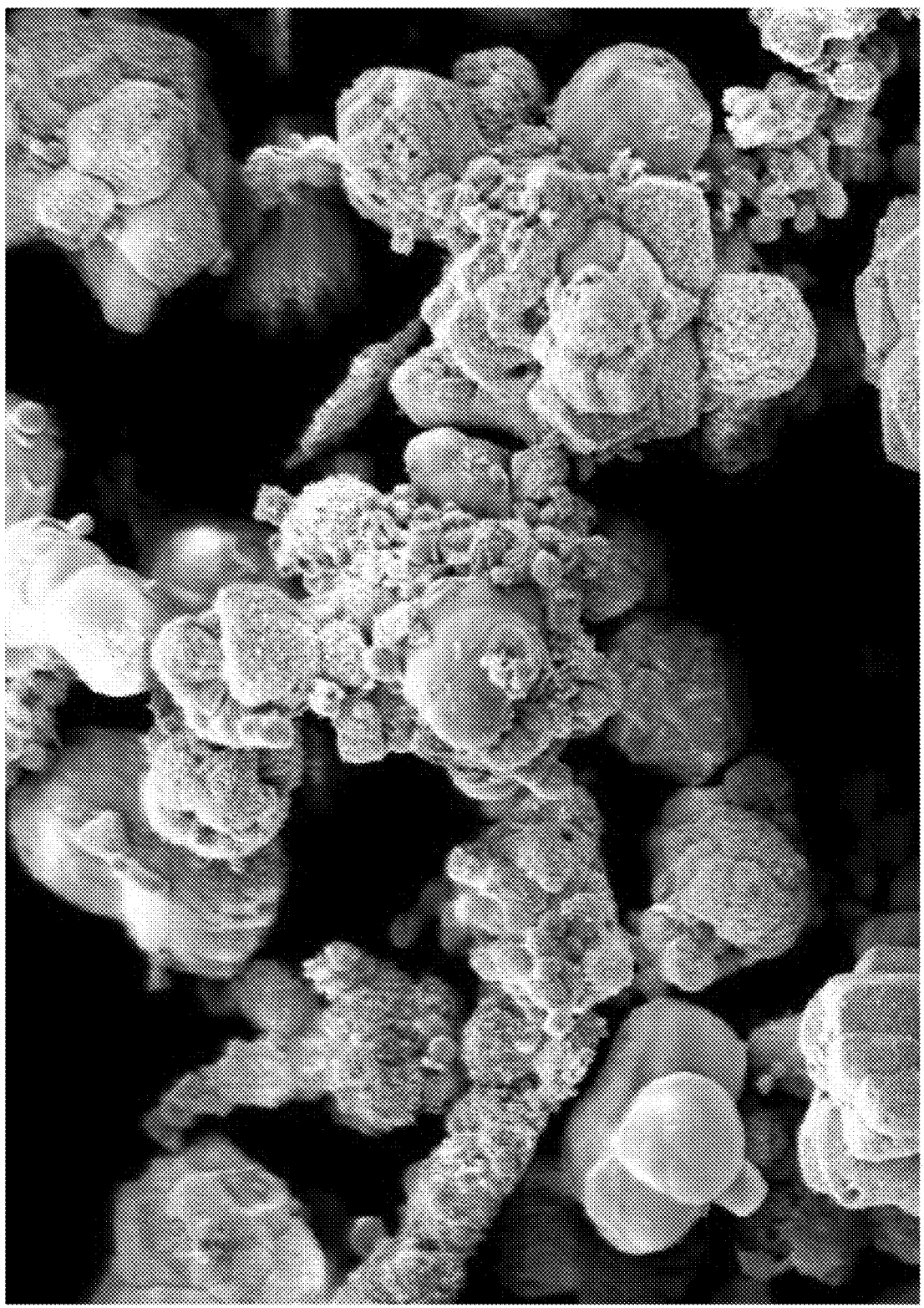
Figure 10D:
Figure 10E:
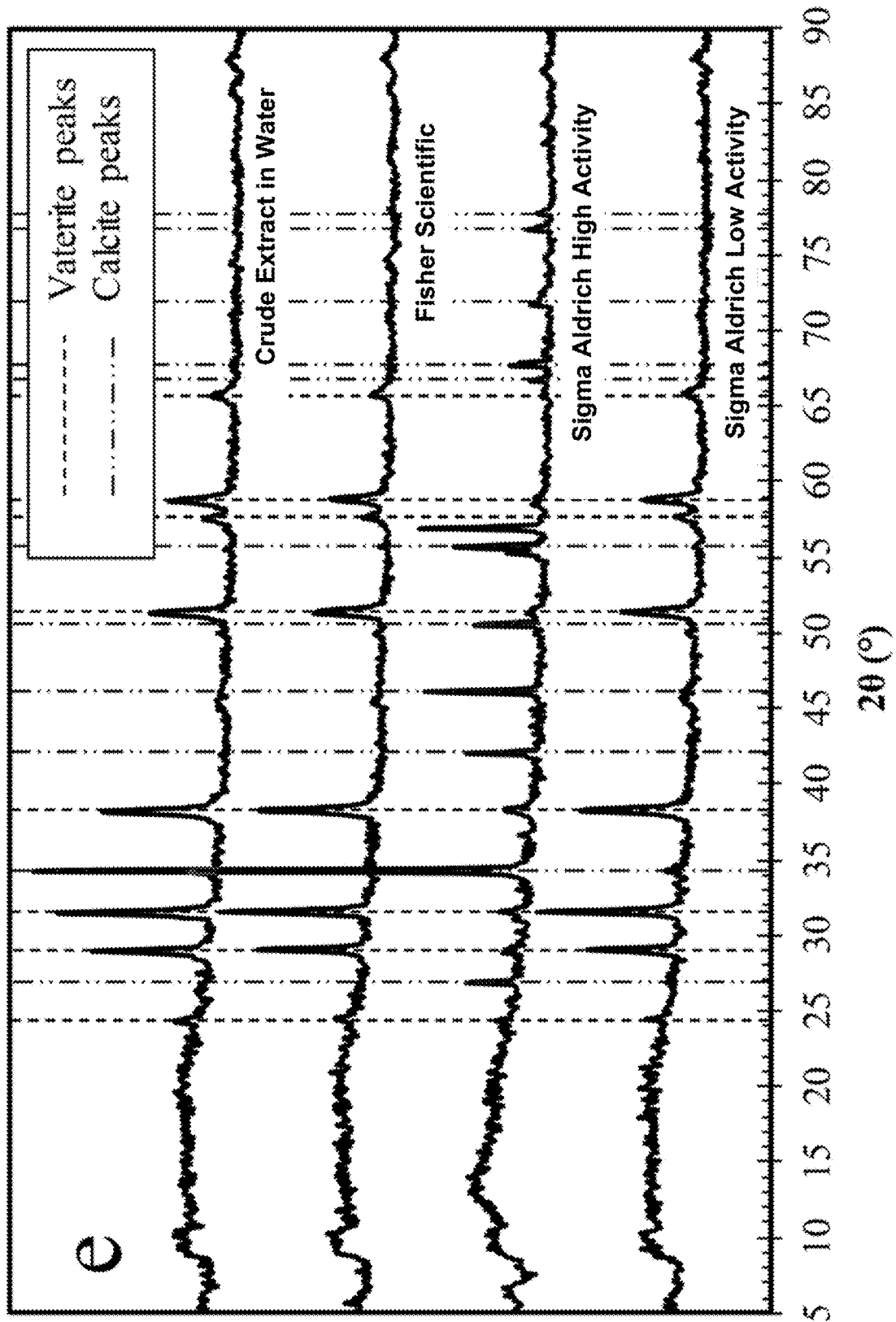

To evaluate the effect of the different enzyme solutions on carbonate precipitation kinetics, pH and dissolved calcium in EICP solutions with a urease activity of 13000 U/l were measured at different time intervals. As illustrated in FIG. 9, the dissolved calcium ion measurements demonstrated that the rate of calcium ion removal from the EICP solution, a proxy for calcium carbonate precipitation, among the solutions with different enzymes are not considerably different. In FIG. 9, dissolved calcium (dashed lines) and pH (solid lines) are measured in EICP solution containing jack bean crude extract (■), Fisher Scientific enzyme (●), high-activity Sigma Aldrich 445 enzyme (▲), and low-activity Sigma Aldrich enzyme (♦). Notably, there was little difference within the initial six hours, which is when EICP-treated soil specimens gain most of their strength based on our empirical observations. In the other words, the precipitation rate is not considerably affected by variation in the enzyme type when initial urease activity in all the tubes were adjusted to 13,000 U/l. The change in pH with time of the different EICP solutions was also similar.

The amount of carbonate precipitation induced by the different enzyme solutions was also similar. Precipitation mass measurements yielded an average precipitation of 3.425 g, 3.518 g, 3.369 g, 449 and 3.387 g after 96 hours in the tubes containing crude extract, Fisher Scientific, high-activity 450 Sigma Aldrich, and low-activity Sigma Aldrich, respectively. It should be noted that, although the precipitates were thoroughly rinsed with DI water and dried until a constant mass achieved, the mass of precipitation in all the tubes was more than the maximum calcium carbonate precipitation of 3.353 g based upon the amount of calcium ion the EICP solution. Potential sources of this extra mass of precipitate could be precipitation of cations imported from the enzyme sources into EICP solution or non-carbonate water-insoluble compounds such as milk and enzyme proteins that precipitated (or salted-out) during the EICP reactions.

Precipitates in the test tubes containing crude extract and Fisher Scientific enzyme clumped together and stuck to the bottom of the tubes such that rigorous hand shaking could not disperse the precipitates into the solution. However, the precipitates in the tubes containing high-activity and low-activity Sigma Aldrich enzymes were easily dispersed in the solution under gentle agitation. The clumping of precipitates in the tubes containing crude extract and Fisher Scientific enzyme may be due to adhesive effect of non-urease proteins which precipitated as a result of interaction between these enzymes' composition and EICP constituents. The crude extract and Fisher Scientific enzyme, which are less refined enzymes, contain compounds (e.g. non-urease proteins, salts, fatty acids, sugars, etc.) which may react with the non-fat milk in EICP solution and result in coagulation of milk proteins, including casein. Non-urease proteins may be also salted out due to change in pH and ion concentrations within EICP reactions. As illustrated in Table 4, the crude extract and Fisher Scientific enzyme introduce much greater amounts of non-urease proteins into the EICP solution.

Morphology and crystal phases of the precipitates obtained in each test tube were evaluated using SEM and XRD. As shown in FIGS. 10a through 10e, it was observed that the precipitates in the tubes containing crude extract, Fisher Scientific, and low-activity Sigma Aldrich enzymes are mainly composed of relatively large spherical vaterite crystal whereas the precipitates in the tubes containing high-activity Sigma Aldrich enzyme are mainly smaller deteriorated calcite crystals agglomerated together. Obtaining vaterite as predominant crystal phase in the tubes of crude extract, Fisher Scientific, and low-activity Sigma Aldrich enzymes might be attributed to higher concentration of organic compounds imported from these enzymes into EICP solution. Crude extract and Fisher Scientific enzyme introduce a higher concentration of proteins into EICP solution (see Table 4). The presence of a protein can modify the rhombohedral face of calcite crystals and reduce their size at low concentration, turn it into spherical calcite crystal at a higher concentration, and at some point, prevents calcite formation.

The crude jack bean extract and the commercial enzymes were used for EICP treatment of granular soil (i.e., sand). The EICP-treated soil was then subject to UCS testing. The treatment solution consisted of 1.0 M urea, 0.67 M $CaCl_2$)-dihydrate, 4 g/l non-fat milk powder, and around 13,000 316 Units of free urease enzyme per liter. One pore volume of treatment solution was percolated into a 5.1 cm-inner diameter closed bottom soil column containing Ottawa 20/30 silica sand (US Silica Company, >99.8% SiO2, emax=0.74, emin=0.50, D50=0.7 mm). Each column contained 350 g sand with a height of around 10.2 cm, resulting in an approximate relative density for the sand prior to treatment of approximately 78 percent. Three specimens were treated for each EICP solution.

The EICP-treated specimens were extracted from their columns after a curing period of around three days at room temperature, soaked in DI water to remove soluble salts, and then subject to UCS testing at a strain rate of 1.27 mm/min. All the specimens were thoroughly soaked in tap water immediately before UCS testing to minimize the effect of capillarity on the measured UCS. Afterwards, around 250 g of each specimen were subjected to carbonate content determination using gravimetric acid digestion. In this method, the treated soil was soaked in 4 M hydrochloric acid to dissolve the carbonate, thoroughly rinsed with tap water, and then dried. The difference between the mass of dry soil before and after acid digestion represents the mass of carbonate precipitation. The mass of precipitation over the mass of dry soil after digestion is reported as the carbonate content of the treated specimen. All of the soil column experiments and associated tests were conducted in triplicate.

Scanning electron microscopy (SEM) was employed to evaluate the morphology of the precipitates from the test tube experiments and the treated soil specimens. X-Ray powder diffraction (XRD) with Co-Kα radiation was applied to identify the mineral crystal phases in the precipitates obtained from each test tube test. Energy dispersive X-ray (EDX) spectroscopy was used for elemental identification of the precipitates in the treated soil specimens. The samples were sputter-coated with gold (Au) prior to SEM imaging and EDX spectroscopy.

Figure 11A:
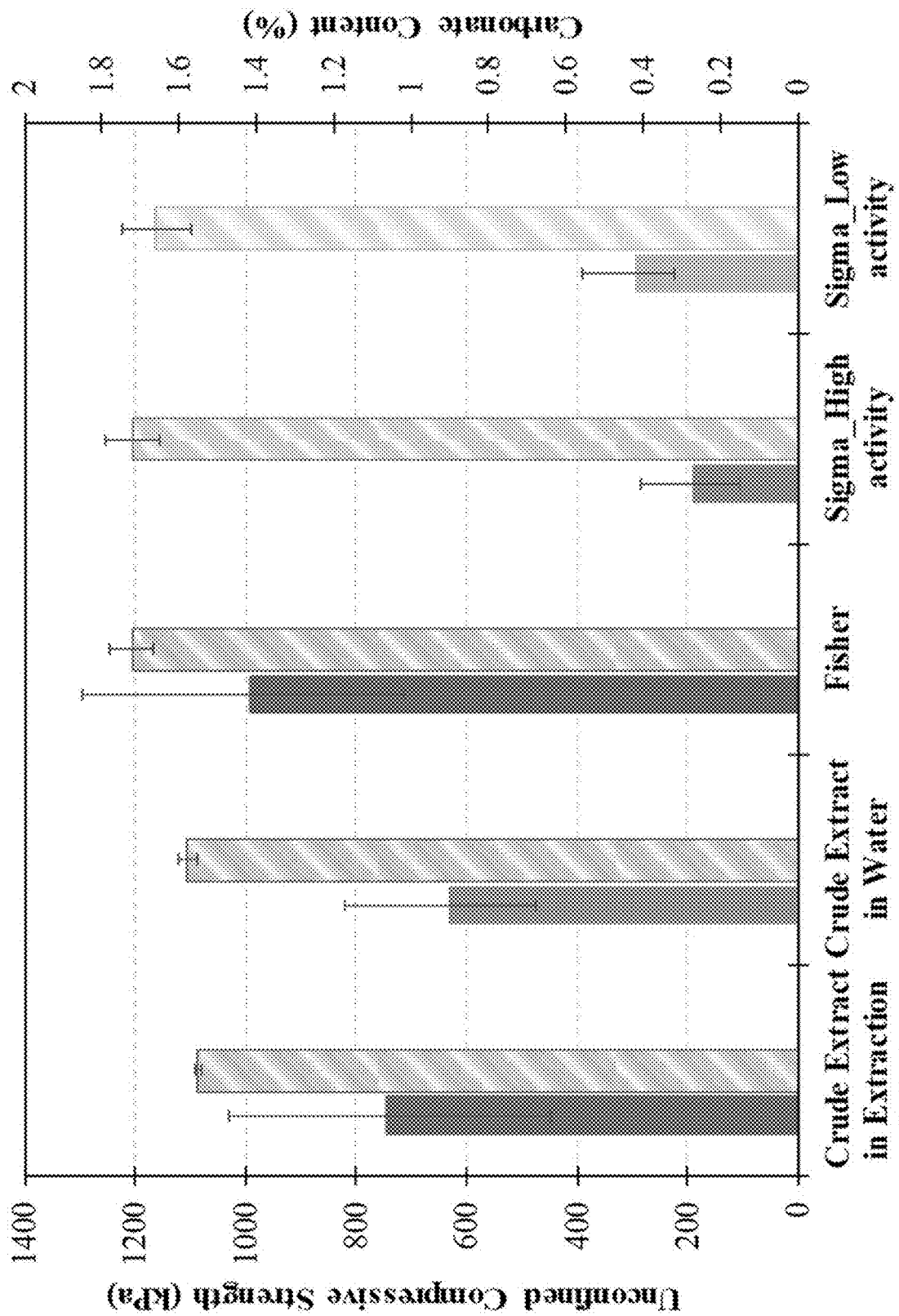
FIG. 11a illustrates unconfined compressive strength and carbonate content for various EICP-treated soil specimens in accordance with various exemplary embodiments.
Figure 11B:
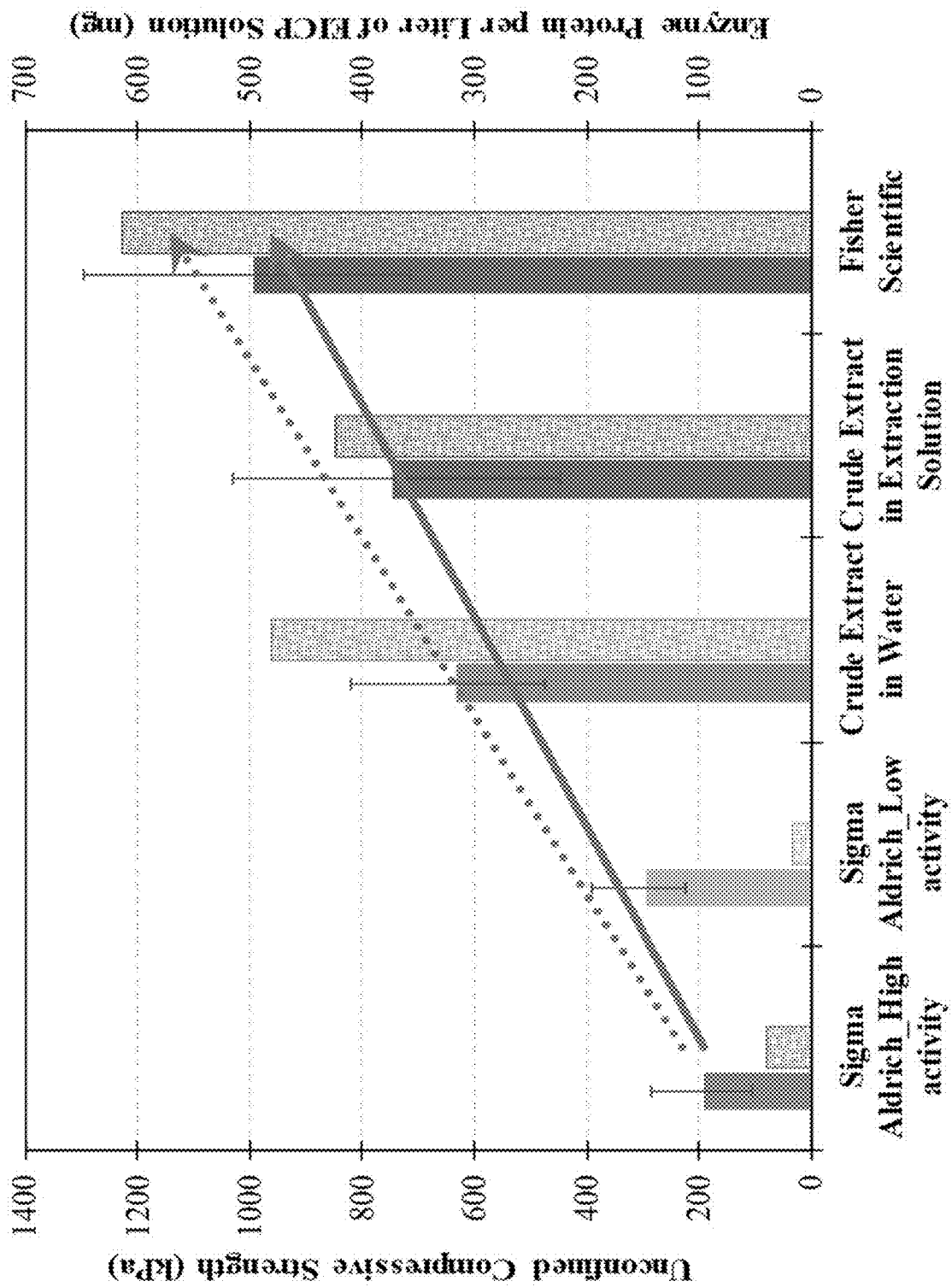
FIG. 11b illustrates unconfined compressive strength and non-urease protein concentration for various EICP-treated soil specimens in accordance with various exemplary embodiments.
Figure 12A:
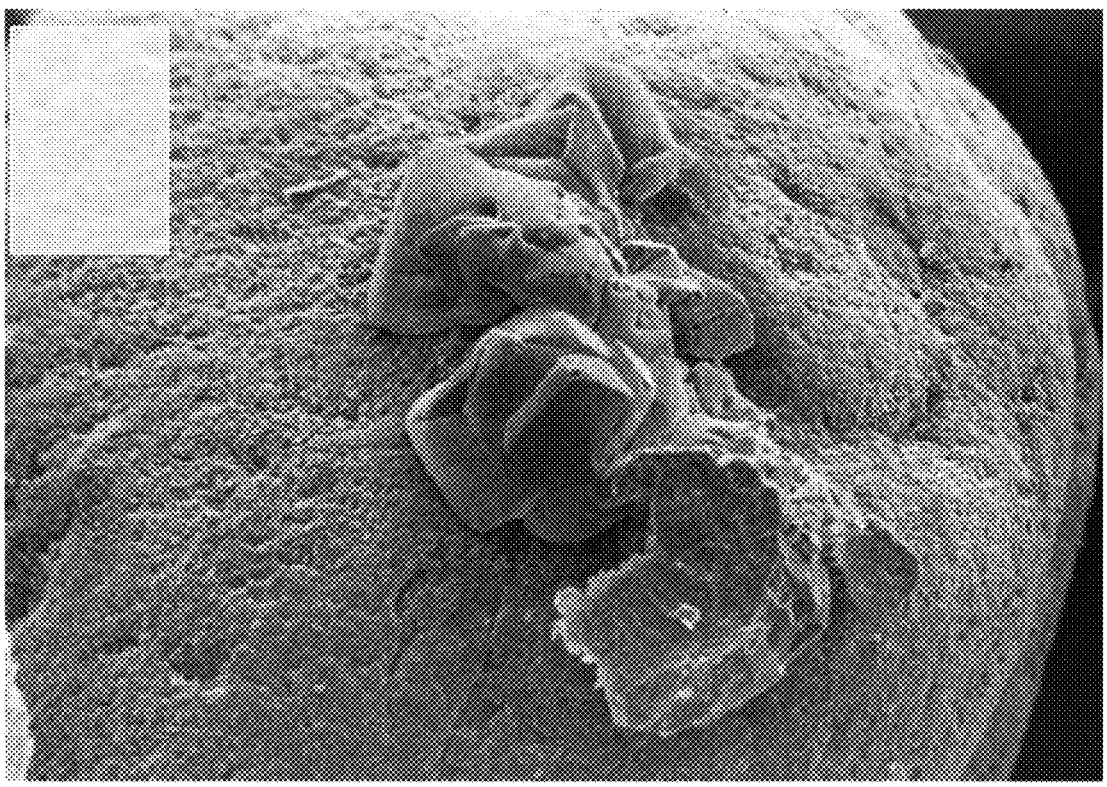
FIGS. 12a-12d illustrate SEM images of soil specimens treated with (a) crude extract, (b) Fisher Scientific 566 enzyme, (c) high-activity Sigma Aldrich, (d) and low-activity Sigma Aldrich.
Figure 12B:
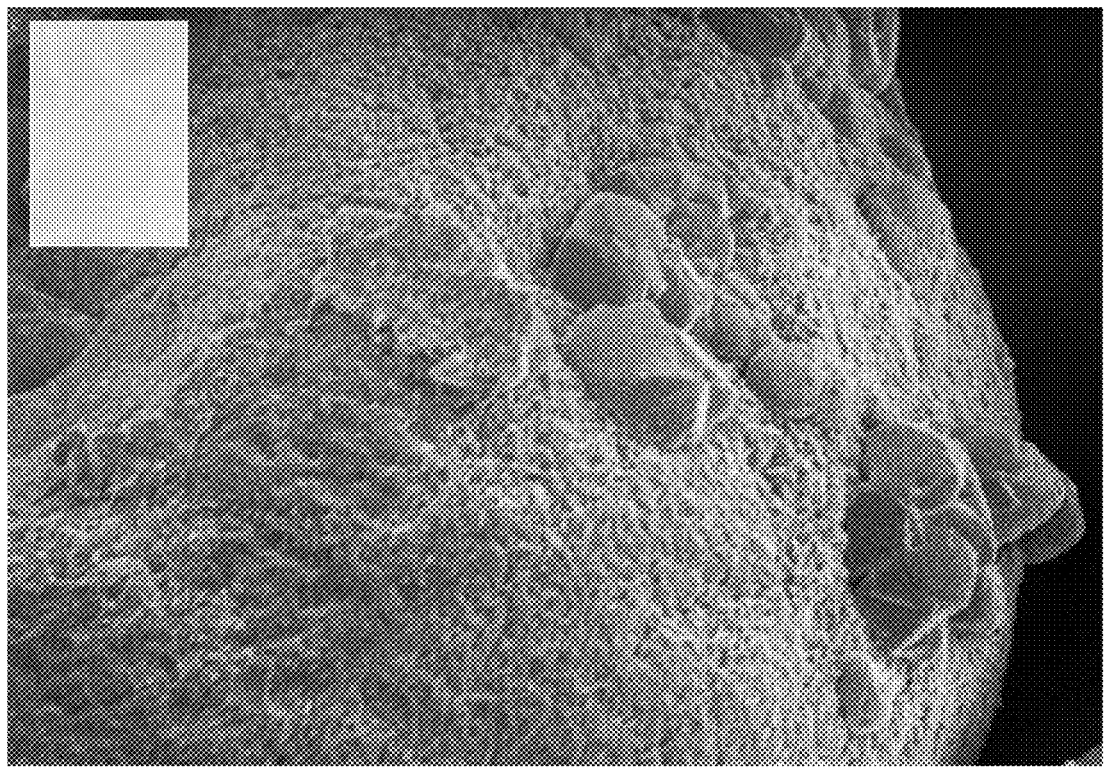
Figure 12C:
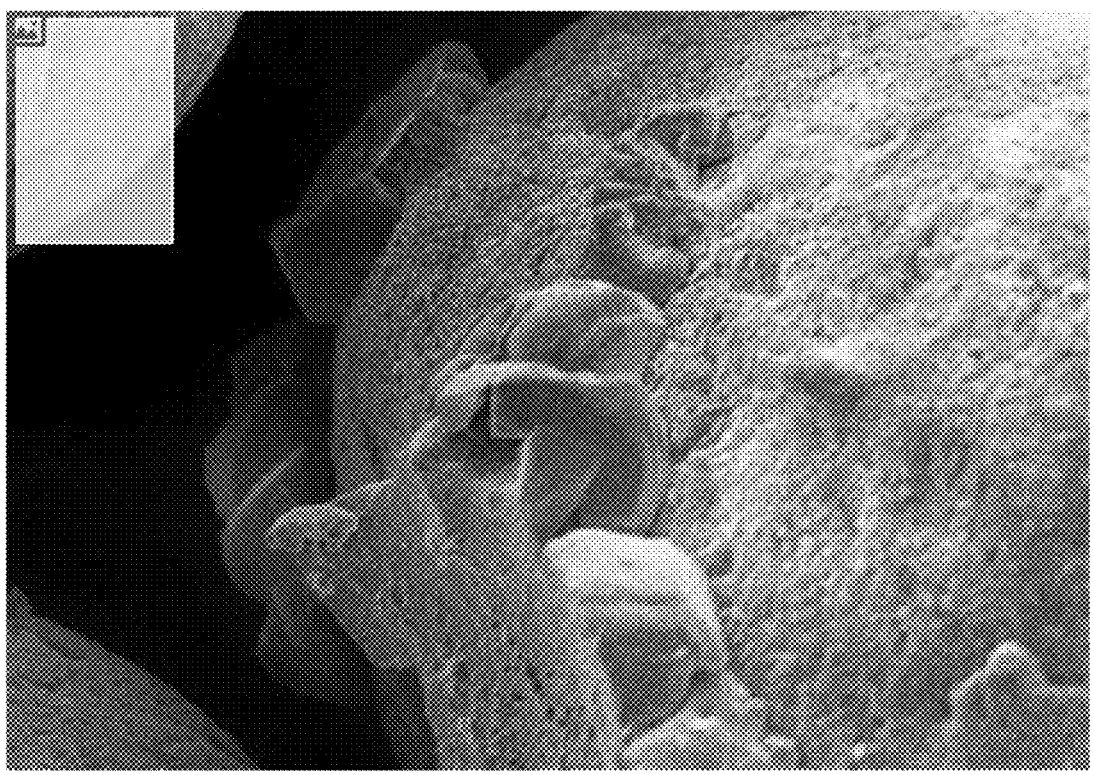
Figure 12D:
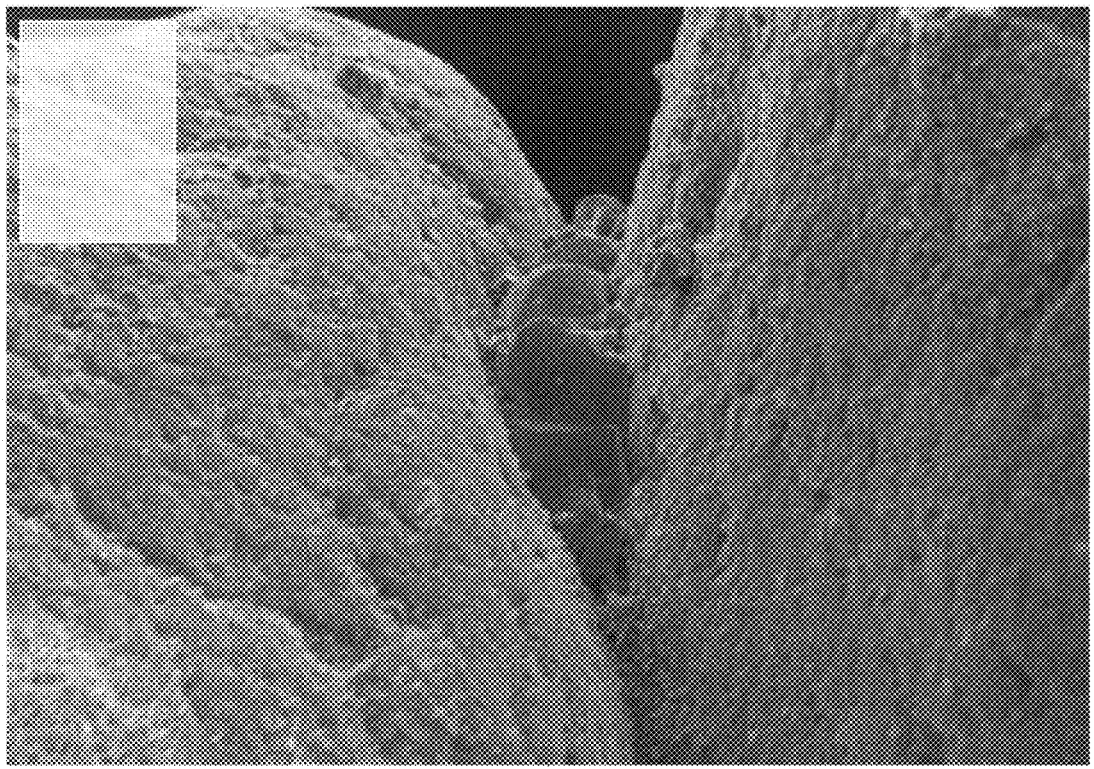

FIG. 11a shows the results of unconfined compression strength testing (filled bars) and the associated carbonate concentrations (hatched bars) for soil specimens treated with each of the five EICP treatment solutions. The carbonate concentrations of the treated soil specimens are similar (approx. 1.5-1.7% w/w), but the strengths are significantly different (ranging from about 200 to about 1000 kPa); this indicates that carbonate content is not the controlling factor in determining strength. FIG. 11b shows the results of the results of unconfined compression strength testing (filled bars) relative to the non-urease protein concentrations (dotted bars). The concentration of non-urease proteins and other impurities associated with urease enzyme (organics/protein additives) correlate with and enhance the strength gain in the EICP-treated soil specimens.

Figure 13:
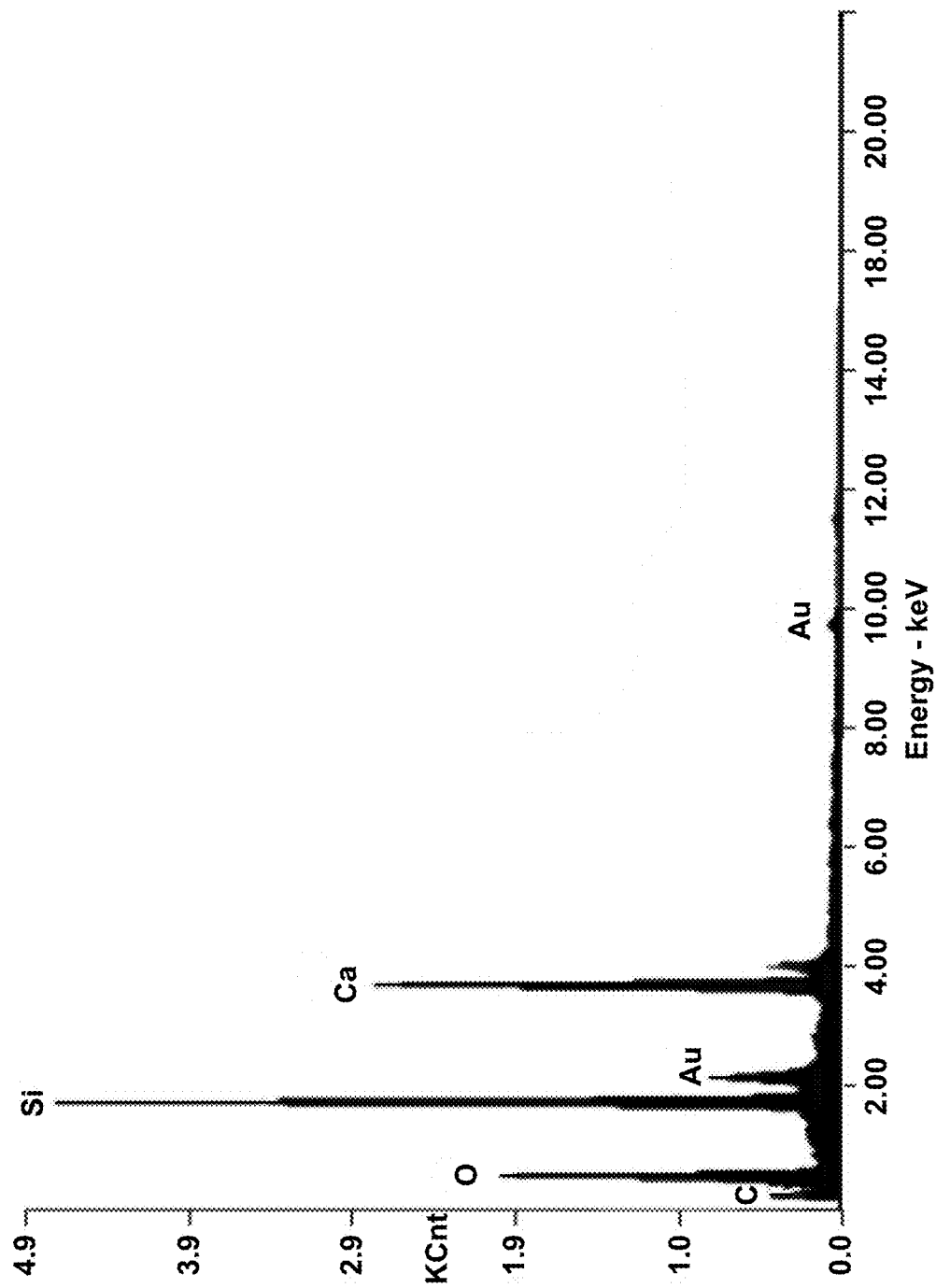
FIG. 13 illustrates EDX analysis of the precipitates on the specimen treated with Fisher Scientific enzyme.

FIG. 12 presents representative SEM images from specimens treated with crude extract and the three commercial enzyme solutions. These SEM images all show the precipitation of rhombohedral crystals characteristic of calcite on the sand particle surfaces. EDX was used to verify the presence of calcite in the treated soil specimens. FIG. 13 presents the EDX spectrograph of the specimen treated using the low-activity Sigma Aldrich enzyme. All the treated specimens showed a similar EDX spectrum. The EDX spectrum in FIG. 13 13 indicates the presence of Ca, O, and C elements. These elements may be attributed to the elemental composition of the calcium carbonate precipitates as it is unlikely that there were any other elements from EICP treatment of a clean silica sand (>99.8% SiO2). These results suggest that the calcium carbonate precipitates that developed in the soil treatment process described herein are calcite phase calcium carbonate. The calcite crystals were relatively large ($\approx$100 µm) in all of the treated specimens.

Unexpectedly and contrary to the test tube experiments, no vaterite was observed in any of the treated soil specimens. The absence of vaterite in the treated sand specimens suggests that the presence of the silica sand particles promotes the precipitation of calcite and/or inhibits the formation of vaterite from the EICP solution. Adhesion of coagulated non-urease proteins to the soil particle surface may promote crystallization of calcite on the soil particle surface. Non-urease proteins may promote calcite crystallization when they are adsorbed at a solid-liquid or air-liquid interface and/or are incorporated in solid structures.

Certain principles of the present disclosure may be utilized in connection with various principles disclosed in: (i) U.S. patent application Ser. No. 15/029,316 filed on Apr. 14, 2016, now U.S. Pat. No. 10,392,767 entitled "MINERAL PRECIPITATION METHODS"; (ii) U.S. patent application Ser. No. 15/029,866 filed on Apr. 15, 2016, now U.S. Pat. No. 10,724,198 entitled "MINERAL PRECIPITATION METHODS"; and/or (iii) U.S. patent application Ser. No. 15/803,700 filed on Nov. 3, 2017, now U.S. Pat. No. 10,563,233 entitled "CEMENTATION METHODS". The contents of each of the foregoing applications are hereby incorporated by reference in their entirety (except for any subject matter disclaimers or disavowals, and except to the extent that the incorporated material is inconsistent with the express disclosure herein, in which case the language in this disclosure controls).

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A method of biocementation comprising:
    treating, via only one treatment cycle, a granular, cohesionless soil with a solution comprising:
        urea;
        urease;
        a source of calcium ions; and
        a source of non-urease proteins, wherein the urea, urease, source of calcium ions, and source of non-urease proteins are provided in effective amounts suitable to cause crystallization of calcium carbonate, and wherein the source of non-urease proteins comprises an enzyme stabilizer; and
    responsive to the only one treatment cycle, forming an enzyme induced carbonate precipitation (EICP) treated soil comprising an unconfined compressive strength of greater than 0.5 MPa and a carbonate content of less than 3% by weight.

2. The method of claim 1, wherein the enzyme stabilizer comprises nonfat milk powder.

3. The method of claim 2, wherein the solution comprises about 4 grams/liter non-fat milk powder.

4. The method of claim 3, wherein the source of calcium ions comprises calcium chloride dihydrate.

5. The method of claim 3, wherein the solution comprises about 0.25 M to about 0.67 M calcium chloride.

6. The method of claim 3, wherein the solution comprises about 0.37 M to about 1 M urea.

7. The method of claim 3, wherein the solution comprises about 0.85 g/L to about 3 g/L urease.

8. The method of claim 1, wherein the enzyme stabilizer comprises casein.

* * * * *